US011560418B2

(12) United States Patent
Kafri

(10) Patent No.: US 11,560,418 B2
(45) Date of Patent: Jan. 24, 2023

(54) METHODS AND COMPOSITIONS FOR MODIFIED FACTOR IX FUSION PROTEINS

(71) Applicant: The University of North Carolina at Chapel Hill, Chapel Hill, NC (US)

(72) Inventor: Tal Kafri, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 838 days.

(21) Appl. No.: 15/769,252

(22) PCT Filed: Oct. 19, 2016

(86) PCT No.: PCT/US2016/057631
§ 371 (c)(1),
(2) Date: Apr. 18, 2018

(87) PCT Pub. No.: WO2017/070167
PCT Pub. Date: Apr. 27, 2017

(65) Prior Publication Data
US 2018/0305439 A1  Oct. 25, 2018

Related U.S. Application Data

(60) Provisional application No. 62/243,726, filed on Oct. 20, 2015.

(51) Int. Cl.
| C12N 7/02 | (2006.01) |
| C07K 14/745 | (2006.01) |
| A01K 67/027 | (2006.01) |
| C12N 9/64 | (2006.01) |
| C12N 15/867 | (2006.01) |
| A61K 38/00 | (2006.01) |

(52) U.S. Cl.
CPC ........ *C07K 14/745* (2013.01); *A01K 67/0275* (2013.01); *C12N 7/025* (2013.01); *C12N 9/644* (2013.01); *C12N 15/867* (2013.01); *C12N 15/8673* (2013.01); *C12Y 304/21022* (2013.01); *A01K 2217/052* (2013.01); *A01K 2217/15* (2013.01); *A01K 2227/105* (2013.01); *A01K 2267/0306* (2013.01); *A01K 2267/0312* (2013.01); *A61K 38/00* (2013.01); *C07K 2317/52* (2013.01); *C07K 2319/30* (2013.01); *C07K 2319/50* (2013.01)

(58) Field of Classification Search
CPC .......................... C12N 15/867; C12N 15/8673
See application file for complete search history.

(56) References Cited

U.S. PATENT DOCUMENTS

| 4,399,216 A | 8/1983 | Axel et al. |
| 4,599,308 A | 7/1986 | Hamer et al. |
| 4,745,051 A | 5/1988 | Smith et al. |
| 4,761,371 A | 8/1988 | Bell et al. |
| 4,877,729 A | 10/1989 | Clark et al. |
| 4,879,236 A | 11/1989 | Smith et al. |
| 4,912,038 A | 3/1990 | Schilling, Jr. et al. |
| 5,175,384 A | 12/1992 | Krimpenfort et al. |
| 5,175,385 A | 12/1992 | Wagner et al. |
| 5,476,995 A | 12/1995 | Clark et al. |
| 5,523,222 A | 6/1996 | Page et al. |
| 5,888,809 A | 3/1999 | Allison |
| 6,344,596 B1 | 2/2002 | Velander et al. |
| 6,686,190 B2 * | 2/2004 | Lau ...................... C07K 14/555 424/204.1 |
| 7,404,956 B2 | 7/2008 | Peters et al. |
| 7,939,632 B2 | 5/2011 | Metzner et al. |
| 8,476,234 B2 | 7/2013 | Fima et al. |
| 8,629,245 B2 | 1/2014 | Georgiou et al. |
| 2013/0274194 A1 | 10/2013 | Dumont et al. |
| 2013/0296534 A1 | 11/2013 | Lee et al. |

FOREIGN PATENT DOCUMENTS

| EP | 0162782 | 11/1985 |
| EP | 0251874 | 1/1988 |
| EP | 0373012 | 6/1990 |
| WO | 84/00560 | 2/1984 |
| WO | 85/05125 | 11/1985 |
| WO | 85/05376 | 12/1985 |
| WO | WO 2006/024694 A2 | 3/2006 |
| WO | WO2013/149167 | * 10/2013 |

OTHER PUBLICATIONS

Kim, V.N., et al. Minimal requirement for a lentivirus vector based on human immunodeficiency virus type I. Journal of Virology, 1998, 72(1):811-816.*

Brooks et al. "Glycoengineered factor IX variants with improved pharmacokinetics and subcutaneous efficacy" *Journal of Thrombosis and Haemostasis* 11:1699-1706 (2013).

International Search Report and the Written Opinion of the International Searching Authority corresponding to International Patent Application No. PCT/US2016/057631 (14 pages) (dated Feb. 9, 2017).

Kumar et al. "Large-Scale Production of Pseudotyped Lentiviral Vectors Using Baculovirus GP64" *Human Gene Therapy* 14:67-77 (2003).

Lin et al. "Generation of a novel factor IX with augmented clotting activities in vitro and in vivo" *Journal of Thrombosis and Haemostasis* 8:1773-1783 (2010).

Shapiro et al. "Recombinant factor IX-Fc fusion protein (rFIXFc) demonstrates safety and prolonged activity in a phase 1/2a study in hemophilia B patients" *Blood* 119(3):666-672 (2012).

(Continued)

*Primary Examiner* — Michael D Burkhart

(74) *Attorney, Agent, or Firm* — Myers Bigel, P.A.

(57) ABSTRACT

The present invention provides Factor IX fusion proteins with higher specific activity and a longer useful clotting function relative to wild type or non-modified Factor IX protein.

5 Claims, 5 Drawing Sheets
Specification includes a Sequence Listing.

(56) References Cited

OTHER PUBLICATIONS

Simioni et al. "X-Linked Thrombophilia with a Mutant Factor IX (Factor IX Padua)" *The New England Journal of Medicine* 361:1671-1675 (2009).
Aiuti et al. "Lentivirus-based Gene Therapy of Hematopoietic Stem Cells in Wiskott-Aldrich Syndrome" Science, 341(6148):1-29 (2013).
Banasik et al. "Integrase-defective lentiviral vectors: progress and applications" Gene Therapy, 17:150-157 (2010).
Bayer et al. "A Large U3 Deletion Causes Increased In Vivo Expression from a Nonintegrating Lentiviral Vector" Molecular Therapy, 16(12):1968-1976 (2008).
Berntorp et al. "Modern haemophilia care" The Lancet, 379(9824):1447-1456 (2012) (Abstract only).
Biffi et al. "Lentiviral Hematopoietic Stem Cell Gene Therapy Benefits Metachromatic Leukodystrophy" Science, 341(6148):1233158-1-1233158-11 (2013).
Cartier et al. "Hematopoietic Stem Cell Gene Therapy with a Lentiviral Vector in X-Linked Adrenoleukodystrophy" 326(5954):818-823 (2009).
Cavazzana-Calvo et al. "Transfusion independence and HMGA2 activation after gene therapy of human beta-thalassaemia" Nature, 467(7313):318-322 (2010).
Cesana et al. "Whole transcriptome characterization of aberrant splicing events induced by lentiviral vector integrations" The Journal of Clinical Investigation, 122(5):1667-1676 (2012).
Chang et al. "Changing residue 338 in human factor IX from arginine to alanine causes an increase in catalytic activity" Journal of Biological Chemistry, 273:12089-12094 (1998).
Cheung et al. "Identification of the endothelial cell binding site for factor IX" Proceedings of the National Academy of Sciences USA, 93:11068-73 (1996).
Cockrell et al. "A Trans-Lentiviral Packaging Cell Line for High-Titer Conditional Self-Inactivating HIV-1 Vectors" Molecular Therapy, 14(2):276-284 (2006).
Cockrell et al. "Gene delivery by lentivirus vectors" Molecular Biotechnology, 36:184-204 (2007).
Coull et al. "The Human Factors YY1 and LSF Repress the Human Immunodeficiency Virus Type 1 Long Terminal Repeat via Recruitment of Histone Deacetylase 1" Journal of Virology, 74(15):6790-6799 (2000).
Darby et al. "Mortality rates, life expectancy, and causes of death in people with hemophilia A or B in the United Kingdom who were not infected with HIV" Blood, 110:815-825 (2007).
Diop et al. "Implementing haemophilia care in Senegal, West Africa" Haemophilia, 20(1):73-77 (2014) (Abstract only).
Graham et al. "The Malmö Polymorphism of Coagulation Factor IX, An Immunologic Polymorphism Due to Dimorphism of Residue 148 That Is in Linkage Disequilibrium with Two Other F.IX Polymorphisms" American Journal of Human Genetics, 42:573-580 (1988).
Kafri et al. "A Packaging Cell Line for Lentivirus Vectors" Journal of Virology, 73(1):576-584 (1999).
Kang et al. "Persistent expression of factor VIII in vivo following nonprimate lentiviral gene transfer" Blood, 106(5):1552-1558 (2005).
Kantor et al. "Notable Reduction in Illegitimate Integration Mediated by a PPT-deleted, Nonintegrating Lentiviral Vector" Molecular Therapy, 19(3):547-556 (2011).
Kao et al. "Incorporation of the factor IX Padua mutation into FIX-Triple improves clotting activity in vitro and in vivo" Thrombosis and Haemostasis, 110:244-256 (2013).
Kim et al. "High Cleavage Efficiency of a 2A Peptide Derived from Porcine Teschovirus-1 in Human Cell Lines, Zebrafish and Mice" PLoS One, 6(4):e18556 (2011).
Lewis et al. "A Common Human Beta Globin Splicing Mutation Modeled in Mice" Blood, 91:2152-2156 (1998).
Li et al. "Alterations of histone modifications by cobalt compounds" Carcinogenesis, 30(7):1243-1251 (2009).
Liu et al. "Titers of lentiviral vectors encoding shRNAs and miRNAs are reduced by different mechanisms that require distinct repair strategies" RNA, 16(7):1328-1339 (2010).
Logan et al. "Integrated Self-Inactivating Lentiviral Vectors Produce Full-Length Genomic Transcripts Competent for Encapsidation and Integration" Journal of Virology, 78(16):8421-8436 (2004).
Ma et al. "A Single-LTR HIV-1 Vector Optimized for Functional Genomics Applications" Molecular Therapy, 10(1):139-149 (2004).
Matthews et al. "Analysis of serial measurements in medical research" BMJ, 300:230-235 (1990).
Matsui et al. "A MicroRNA-regulated and GP64-pseudotyped Lentiviral Vector Mediates Stable Expression of FVIII in a Murine Model of Hemophilia A" Molecular Therapy, 19(4):723-730 (2011).
May et al. "Therapeutic haemoglobin synthesis in beta-thalassaemic mice expressing lentivirus-encoded human beta-globin" Nature, 406(6791):82-86 (2000) (Abstract only).
Metzner et al. "Genetic fusion to albumin improves the pharmacokinetic properties of factor IX" Thrombosis and Haemostasis, 102(4):634-644 (2009).
Mimnaugh et al. "Rapid Deubiquitination of Nucleosomal Histones in Human Tumor Cells Caused by Proteasome Inhibitors and Stress Response Inducers:? Effects on Replication, Transcription, Translation, and the Cellular Stress Response" Biochemistry, 36(47):14418-14429 (1997) (Abstract only).
Miyoshi et al. "Development of a Self-Inactivating Lentivirus Vector" Journal of Virology, 72(10):8150-8157 (1998).
Montini et al. "Hematopoietic stem cell gene transfer in a tumor-prone mouse model uncovers low genotoxicity of lentiviral vector integration" Nature Biotechnology, 24(6):687-696 (2006) (Abstract only).
Naldini, Luigi "Ex vivo gene transfer and correction for cell-based therapies" Nature Reviews Genetics, 12(5):301-315 (2011) (Abstract only).
Osley, Mary Ann "Regulation of histone H2A and H2B ubiquitylation" Briefings in Functional Genomics, 5(3):179-189 (2006).
Ou et al. "Role of flanking E box motifs in human immunodeficiency virus type 1 TATA element function" Journal of Virology, 68(11):7188-7199 (1994).
Peters et al. "Prolonged activity of factor IX as a monomeric Fc fusion protein" Blood, 115:2057-2064 (2010).
Peters et al. "Biochemical and functional characterization of a recombinant monomeric factor VIII-Fc fusion protein" Journal of Thrombosis and Haemostasis, 11:132-141 (2013).
Pfeifer et al. "Transduction of Liver Cells by Lentiviral Vectors: Analysis in Living Animals by Fluorescence Imaging" Molecular Therapy, 3(3):319-322 (2001).
Poon et al. "Human Immunodeficiency Virus Type 1 (HIV-1) Vpr Enhances Expression from Unintegrated HIV-1 DNA" Journal of Virology, 77(7):3962-3972 (2003).
Powell et al. "Phase 3 Study of Recombinant Factor IX Fc Fusion Protein in Hemophilia B" The New England Journal of Medicine, 369(24):2313-2323 (2013).
Romero et al. "The human ankyrin 1 promoter insulator sustains gene expression in a beta-globin lentiviral vector in hematopoietic stem cells" Molecular Therapy—Methods & Clinical Development, 2(15012):1-9 (2015).
Roth et al. "Human recombinant factor IX: safety and efficacy studies in hemophilia B patients previously treated with plasma-derived factor IX concentrates" Blood, 98(13):3600-3606 (2001).
Sabatino et al. "Animal Models of Hemophilia" Progress in Molecular Biology and Translational Science, 105:151-209 (2012).
Schauber et al. "Lentiviral vectors pseudotyped with baculovirus gp64 efficiently transduce mouse cells in vivo and show tropism restriction against hematopoietic cell types in vitro" Gene Therapy, 11:266-275 (2004).
Schulte, Stefan "Half-life extension through albumin fusion technologies" Thrombosis Research, 124(Suppl 2):S6-S8 (2009) (Abstract only).
Suwanmanee et al. "Integration-deficient Lentiviral Vectors Expressing Codon-optimized R338L Human FIX Restore Normal Hemostasis in Hemophilia B Mice" Molecular Therapy, 22(3):567-574 (2014).
Svarovskaia et al. "Azido-Containing Diketo Acid Derivatives Inhibit Human Immunodeficiency Virus Type 1 Integrase In Vivo and Influence the Frequency of Deletions at Two-Long-Terminal-Repeat-Circle Junctions" Journal of Virology, 78(7):3210-3222 (2004).

(56) References Cited

OTHER PUBLICATIONS

Tareen et al. "Design of a Novel Integration-deficient Lentivector Technology That Incorporates Genetic and Posttranslational Elements to Target Human Dendritic Cells" Molecular Therapy, 22(3):575-587 (2014).

Valentino, Leonard A. "Recombinant FIXFc: a novel therapy for the royal disease?" Expert Opinion on Biological Therapy, 11(10):1361-1368 (2011).

Van Cott et al. "Haemophilic factors produced by transgenic livestock: abundance can enable alternative therapies worldwide" Haemophilia, 10(4):70-77 (2004).

Walsh et al. "Hemophilia clinical gene therapy: brief review" Translational Research, 161(4):307-312 (2013) (Abstract only).

Wang et al. "Identification and characterization of two critical sequences in SV40PolyA that activate the green fluorescent protein reporter gene" Genetics and Molecular Biology, 34(3):396-405 (2011).

Wanisch et al. "Integration-deficient Lentiviral Vectors: A Slow Coming of Age" Molecular Therapy, 17(8):1316-1332 (2009).

White et al. "Clinical evaluation of recombinant factor IX" Seminars in Hematology, 35(2 Suppl. 2):33-38 (1998) (Abstract only).

Xu et al. "Generation of a Stable Cell Line Producing High-Titer Self-Inactivating Lentiviral Vectors" Molecular Therapy, 3(1):97-104 (2001).

Yu et al. "Self-inactivating retroviral vectors designed for transfer of whole genes into mammalian cells" Proceedings of the National Academy of Sciences USA, 83(10):3194-3198 (1986).

Zhang et al. "Protein Kinase PKR Plays a Stimulus- and Virus-Dependent Role in Apoptotic Death and Virus Multiplication in Human Cells" Journal of Virology, 81(15):8192-8200 (2007).

Zhang et al. "Loss of Protein Kinase PKR Expression in Human HeLa Cells Complements the Vaccinia Virus E3L Deletion Mutant Phenotype by Restoration of Viral Protein Synthesis" Journal of Virology, 82(2):840-848 (2008).

Zhou et al. "Histone H2A Monoubiquitination Represses Transcription by Inhibiting RNA Polymerase II Transcriptional Elongation" Molecular Cell, 29(1):69-80 (2008).

Zhu et al. "A Histone H2A Deubiquitinase Complex Coordinating Histone Acetylation and H1 Dissociation in Transcriptional Regulation" Molecular Cell, 27(4):609-621 (2007).

Hu et al. "Superior lentiviral vectors designed for BSL-0 environment abolish vector mobilization" Gene Therapy, 25:454-472 (2018).

Coffin et al. "Experimental Applications" Retroviruses, Cold Spring Harbor Laboratory Press (8 pages) (1997).

Mitta et al. "Detailed design and comparative analysis of protocols for optimized production of high-performance HIV-1-derived lentiviral particles" Metabolic Engineering, 7:426-436 (2005).

Han et al. "Improved lentiviral vector titers from a multi-gene knockout packaging line" Molecular Therapy: Oncolytics, 23:582-592 (2021).

Han et al. "β-Globin Lentiviral Vectors Have Reduced Titers due to Incomplete Vector RNA Genomes and Lowered Virion Production" Stem Cell Reports, 16:198-211 (2021).

\* cited by examiner

```
                        SEQUENCE LISTING

<160> NUMBER OF SEQ ID NOS: 7

<210> SEQ ID NO 1
<211> LENGTH: 415
<212> TYPE: PRT
<213> ORGANISM: Homo sapiens

<400> SEQUENCE: 1

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240
```

```
Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 2
<211> LENGTH: 227
<212> TYPE: PRT
<213> ORGANISM: Homo sapiens

<400> SEQUENCE: 2

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Arg Leu Ala Val Glu
145                 150                 155                 160

Trp Glu Ser Asn Gly Gln Pro Glu Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
        210                 215                 220

Pro Gly Lys
225

<210> SEQ ID NO 3
<211> LENGTH: 21
<212> TYPE: PRT
<213> ORGANISM: Artificial
<220> FEATURE:
<223> OTHER INFORMATION: Amino acid linker sequence

<400> SEQUENCE: 3

Ser Val Ser Gln Thr Ser Lys Leu Thr Arg Ala Glu Thr Val Phe Pro
1               5                   10                  15

Asp Val Asp Gly Ser
            20

<210> SEQ ID NO 4
<211> LENGTH: 4
<212> TYPE: PRT
<213> ORGANISM: Artificial
<220> FEATURE:
<223> OTHER INFORMATION: Amino acid linker sequence

<400> SEQUENCE: 4

Gly Gly Gly Ser
1

<210> SEQ ID NO 5
<211> LENGTH: 18
<212> TYPE: PRT
<213> ORGANISM: Artificial
<220> FEATURE:
<223> OTHER INFORMATION: Amino acid linker sequence

<400> SEQUENCE: 5

Gly Ser Thr Ser Gly Ser Gly Lys Pro Gly Ser Gly Glu Gly Ser Thr
1               5                   10                  15

Lys Gly

<210> SEQ ID NO 6
<211> LENGTH: 948
<212> TYPE: PRT
<213> ORGANISM: Artificial
<220> FEATURE:
<223> OTHER INFORMATION: Recombinant FIX fusion protein sequence

<400> SEQUENCE: 6

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65              70                  75                  80

Thr Glu Arg Thr Thr Glu Phe Trp Lys Gln Tyr Val Asp Gly Asp Gln
                85                  90                  95

```
Cys Glu Ser Asn Pro Cys Leu Asn Gly Gly Ser Cys Lys Asp Asp Ile
                100                 105                 110
Asn Ser Tyr Glu Cys Trp Cys Pro Phe Gly Phe Glu Gly Lys Asn Cys
            115                 120                 125
Glu Leu Asp Val Thr Cys Asn Ile Lys Asn Gly Arg Cys Glu Gln Phe
        130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
    290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Leu
    370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr Ser Val Ser
    450                 455                 460
Gln Thr Ser Lys Leu Thr Arg Ala Glu Thr Val Phe Pro Asp Val Asp
465                 470                 475                 480
Gly Ser Asp Lys Thr His Thr Cys Pro Pro Cys Pro Ala Pro Glu Leu
                485                 490                 495
Leu Gly Gly Pro Ser Val Phe Leu Phe Pro Pro Lys Pro Lys Asp Thr
            500                 505                 510
Leu Met Ile Ser Arg Thr Pro Glu Val Thr Cys Val Val Val Asp Val
```

-continued

```
                515                 520                 525
Ser His Glu Asp Pro Glu Val Lys Phe Asn Trp Tyr Val Asp Gly Val
530                 535                 540

Glu Val His Asn Ala Lys Thr Lys Pro Arg Glu Glu Gln Tyr Asn Ser
545                 550                 555                 560

Thr Tyr Arg Val Val Ser Val Leu Thr Val Leu His Gln Asp Trp Leu
                565                 570                 575

Asn Gly Lys Glu Tyr Lys Cys Lys Val Ser Asn Lys Ala Leu Pro Ala
                580                 585                 590

Pro Ile Glu Lys Thr Ile Ser Lys Ala Lys Gly Gln Pro Arg Glu Pro
                595                 600                 605

Gln Val Tyr Thr Leu Pro Pro Ser Arg Asp Glu Leu Thr Lys Asn Gln
                610                 615                 620

Val Ser Leu Thr Cys Leu Val Lys Gly Phe Tyr Pro Ser Arg Leu Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
                660                 665                 670

Thr Val Asp Lys Ser Arg Trp Gln Gln Gly Asn Val Phe Ser Cys Ser
                675                 680                 685

Val Met His Glu Ala Leu His Asn His Tyr Thr Gln Lys Ser Leu Ser
690                 695                 700

Leu Ser Pro Gly Lys Gly Gly Ser Gly Gly Ser Gly Gly Gly
705                 710                 715                 720

Ser Asp Lys Thr His Thr Cys Pro Pro Cys Pro Ala Pro Glu Leu Leu
                725                 730                 735

Gly Gly Pro Ser Val Phe Leu Phe Pro Pro Lys Pro Lys Asp Thr Leu
                740                 745                 750

Met Ile Ser Arg Thr Pro Glu Val Thr Cys Val Val Val Asp Val Ser
                755                 760                 765

His Glu Asp Pro Glu Val Lys Phe Asn Trp Tyr Val Asp Gly Val Glu
                770                 775                 780

Val His Asn Ala Lys Thr Lys Pro Arg Glu Glu Gln Tyr Asn Ser Thr
785                 790                 795                 800

Tyr Arg Val Val Ser Val Leu Thr Val Leu His Gln Asp Trp Leu Asn
                805                 810                 815

Gly Lys Glu Tyr Lys Cys Lys Val Ser Asn Lys Ala Leu Pro Ala Pro
                820                 825                 830

Ile Glu Lys Thr Ile Ser Lys Ala Lys Gly Gln Pro Arg Glu Pro Gln
                835                 840                 845

Val Tyr Thr Leu Pro Pro Ser Arg Asp Glu Leu Thr Lys Asn Gln Val
                850                 855                 860

Ser Leu Thr Cys Leu Val Lys Gly Phe Tyr Pro Ser Arg Leu Ala Val
865                 870                 875                 880

Glu Trp Glu Ser Asn Gly Gln Pro Glu Asn Asn Tyr Lys Thr Thr Pro
                885                 890                 895

Pro Val Leu Asp Ser Asp Gly Ser Phe Phe Leu Tyr Ser Lys Leu Thr
                900                 905                 910

Val Asp Lys Ser Arg Trp Gln Gln Gly Asn Val Phe Ser Cys Ser Val
                915                 920                 925

Met His Glu Ala Leu His Asn His Tyr Thr Gln Lys Ser Leu Ser Leu
930                 935                 940
```

Ser Pro Gly Lys
945

<210> SEQ ID NO 7
<211> LENGTH: 2847
<212> TYPE: DNA
<213> ORGANISM: Artificial
<220> FEATURE:
<223> OTHER INFORMATION: Recombinant FIX fusion protein coding sequence

<400> SEQUENCE: 7

| | |
|---|---|
| atgcagcgcg tgaacatgat catggccgag agccctggcc tgatcaccat ctgcctgctg | 60 |
| ggctacctgc tgagcgccga gtgcaccgtg ttcctggacc acgagaacgc caacaagatc | 120 |
| ctgaaccggc caagagata caacagcggc aagctggagg agttcgtgca gggcaacctg | 180 |
| gagagggagt gcatggagga gaagtgcagc ttcgaggagg ccagggaagt gttcgagaac | 240 |
| accgagcgga ccaccgagtt ctggaagcag tacgtggacg gcgaccagtg cgagagcaac | 300 |
| ccttgcctga acggcggcag ctgcaaggac gacatcaaca gctacgagtg ctggtgccct | 360 |
| ttcggcttcg agggcaagaa ctgcgagctg gacgtgacct gcaacatcaa gaacggccgc | 420 |
| tgcgagcagt tctgcaagaa cagcgccgac aacaaagtgg tgtgtagctg caccgagggc | 480 |
| tacagactgg ccgagaacca gaagagctgc gagcccgccg tgcccttccc ctgcggcaga | 540 |
| gtgagcgtgt cccagaccag caagctgacc agagccgaga ccgtgttccc cgacgtggac | 600 |
| tacgtgaata gcaccgaggc cgagaccatc ctggacaaca tcacccagag cacccagtcc | 660 |
| ttcaacgact tcaccagagt tgtgggcggc gaggacgcca agcccggcca gttcccctgg | 720 |
| caggtggtgc tgaacggcaa agtggatgcc ttctgcggcg gcagcatcgt gaacgagaag | 780 |
| tggatcgtga cagccgccca ctgcgtggag accggcgtga agatcaccgt ggtggccggc | 840 |
| gaacacaata tcgaggagac cgagcacacc gagcagaagc ggaacgtcat ccggattatc | 900 |
| ccccaccaca actacaacgc cgccatcaac aagtacaacc acgacatcgc cctgctggag | 960 |
| ctggacgagc tctggtgct gaatagctac gtgacccca tctgcatcgc cgacaaggag | 1020 |
| tacaccaaca tcttcctgaa gttcggcagc ggctacgtgt ccggctgggg cagagtgttc | 1080 |
| cacaagggca agcgccct ggtgctgcag tacctgagag tgcccctggt ggacagagcc | 1140 |
| acctgcctgt tgagcaccaa gttcaccatc tacaacaaca tgttctgcgc cggcttccac | 1200 |
| gagggcggca gagacagctg ccagggcgac agcggcggac cccacgtgac agaggtggaa | 1260 |
| ggcaccagct ttctgaccgg catcatcagc tggggcgagg aatgcgccat gaaggggaag | 1320 |
| tacggcatct acaccaaggt gtccagatac gtgaactgga tcaaagaaaa gaccaagctg | 1380 |
| acatctgtgt ctcagacctc taagctgaca cgggccgaaa ctgtgtttcc tgatgtggac | 1440 |
| ggcagcgaca agacccacac ctgtcctcca tgtcccgccc ctgaactgct gggcggacct | 1500 |
| agcgtgttcc tgttcccccc aaagcccaag gacaccctga tgatcagccg gacccccgaa | 1560 |
| gtgacctgcg tggtggtgga tgtgtcccac gaggaccctg aagtgaagtt caattggtat | 1620 |
| gtggatggcg tggaagtgca caacgccaag acaaagccca gagaggaaca gtacaactcc | 1680 |
| acctaccggg tggtgtccgt gctgaccgtg ctgcaccagg actggctgaa tggcaaagag | 1740 |
| tataagtgca aagtgtccaa caaggccctg cctgccccca tcgagaaaac catcagcaag | 1800 |
| gccaagggcc agccccgcga acccagggta tacacactgc ccctagcag ggacgagctg | 1860 |
| accaagaacc aggtgtccct gacctgtctc gtgaagggct tctaccctag ccggctggcc | 1920 |
| gtggaatggg agagcaatgg ccagcccgag aacaattaca agaccacccc ccctgtgctg | 1980 |

```
gacagcgacg gctcattctt cctgtacagc aaactgaccg tggacaagag ccggtggcag    2040
cagggcaatg tgttcagctg tagcgtgatg cacgaggccc tgcacaacca ctacacccag    2100
aagtctctga gcctgagccc cggcaagggc ggaggaagtg ggggaggatc tggcggcggc    2160
tccgataaga cacatacctg ccccccttgc cctgccccag agctgctggg aggcccttct    2220
gtgtttctgt ttccacctaa gcctaaagat acactgatga tctcccgcac acctgaagtg    2280
acatgtgtgg tggtggacgt gtcacatgaa gatccagaag tgaagtttaa ttggtacgtg    2340
gacggggtgg aagtgcataa tgctaagacc aaacccgggg aagaacagta taacagcaca    2400
tacagagtgg tgtctgtgct gacagtgctg catcaggatt ggctgaacgg gaaagaatac    2460
aaatgtaaag tgtctaacaa agctctgccc gctcctatcg aaaagacaat ctccaaggct    2520
aaaggacagc ccagagaacc tcaggtgtac acactgcctc catcccgcga cgagctgaca    2580
aaaaatcagg tgtcactgac atgcctcgtg aagggggtttt atccatctag gctggctgtg    2640
gaatgggaat ccaacggaca gcctgaaaac aactataaga caacacctcc cgtgctggac    2700
tccgatggct cattttttct gtattccaag ctgactgtgg ataagtccag atggcagcag    2760
ggaaacgtgt tctcctgttc tgtgatgcat gaagctctgc ataatcatta tacccagaaa    2820
agcctgtccc tgtcccctgg caagtga                                        2847
```

US 11,560,418 B2

METHODS AND COMPOSITIONS FOR MODIFIED FACTOR IX FUSION PROTEINS

STATEMENT OF PRIORITY

This application is a 35 U.S.C. § 371 national phase application of International Application Serial No. PCT/US2016/057631, filed Oct. 19, 2016, which claims the benefit, under 35 U.S.C. § 119(e), of U.S. Provisional Patent Application No. 62/243,726, filed Oct. 20, 2015, the entire contents of which are incorporated by reference herein.

STATEMENT OF GOVERNMENT SUPPORT

This invention was made with government support under Grant No. 5R01DK058702-13, awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-759_ST25.txt, 18,733 bytes in size, generated on Apr. 17, 2018 and filed via EFS-Web, is provided in lieu of a paper copy. This Sequence Listing is incorporated by reference into the specification for its disclosures.

FIELD OF THE INVENTION

The invention pertains to Factor IX fusion proteins containing modifications in the amino acid sequence of the Factor IX protein, as well as nucleic acid constructs encoding the Factor IX fusion proteins. The invention also pertains to modifications in the nucleotide sequence of the Factor IX protein, including modifications that do not change the amino acid sequence (codon-optimization).

BACKGROUND OF THE INVENTION

Factor IX is commercially available as both a plasma-derived product (Mononine®) and a recombinant protein (Benefix®). Mononine® has the disadvantage that there is a potential to transmit disease through contamination with bacteria and viruses (such as HIV, hepatitis) which are carried through the purification procedure. The use of recombinant protein (e.g., Benefix®) avoids these problems. However, the pharmacokinetic properties of recombinant Factor IX (rFactor IX, e.g., Benefix®) do not compare well with the properties of human plasma-derived Factor IX (pdFactor IX, e.g., Mononine®) after intravenous (i.v.) bolus infusion in laboratory animal model systems and in humans. Due to the less favorable pharmacokinetic properties of rFactor IX, generally 20-30% higher doses of rFactor IX are required to achieve the same procoagulant activity level as pdFactor IX (White et al. (April 1998) *Seminars in Hematology* vol. 35, no. 2 Suppl. 2: 33-38; Roth et al. (Dec. 15, 2001) *Blood* vol. 98 (13): 3600-3606).

The present invention provides modified Factor IX (FIX) fusion proteins that have higher specific activity, longer useful clotting function and longer half life in a subject's blood, relative to wild type or non-modified Factor IX protein. The present invention also provides a Factor IX protein produced from a modified Factor IX nucleotide sequence that enhances Factor IX protein production in vivo and in vitro.

SUMMARY OF THE INVENTION

In one aspect, the present invention provides a recombinant Factor IX (FIX) fusion protein comprising in the following order: a) a FIX protein comprising a R338L substitution wherein said amino acid substitution is made at a position in reference to the amino acid sequence of SEQ ID NO:1 (wild type human FIX); b) a first linker sequence comprising a cleavage site; c) a first immunoglobulin (Ig) Fc domain; d) a second linker sequence; and e) a second immunoglobulin Fc domain, wherein said first Ig Fc domain and said second Ig Fc domain are associated via one or more disulfide bonds.

In an additional aspect, the present invention provides a codon-optimized nucleotide sequence encoding the Factor IX protein of this invention.

In an additional aspect, the present invention provides a method of treating a bleeding disorder in a subject in need thereof, comprising administering to the subject an effective amount of the Factor IX fusion protein, nucleic acid molecule, vector and/or cell of this invention.

Additionally provided is a method of increasing the bioavailablity of a Factor IX protein in a subject, comprising administering to the subject an effective amount of the Factor IX fusion protein, nucleic acid molecule, vector and/or cell of this invention.

Further aspects, features and advantages of this invention will become apparent from the detailed description of the embodiments which follow.

DETAILED DESCRIPTION OF THE INVENTION

Figure 1:
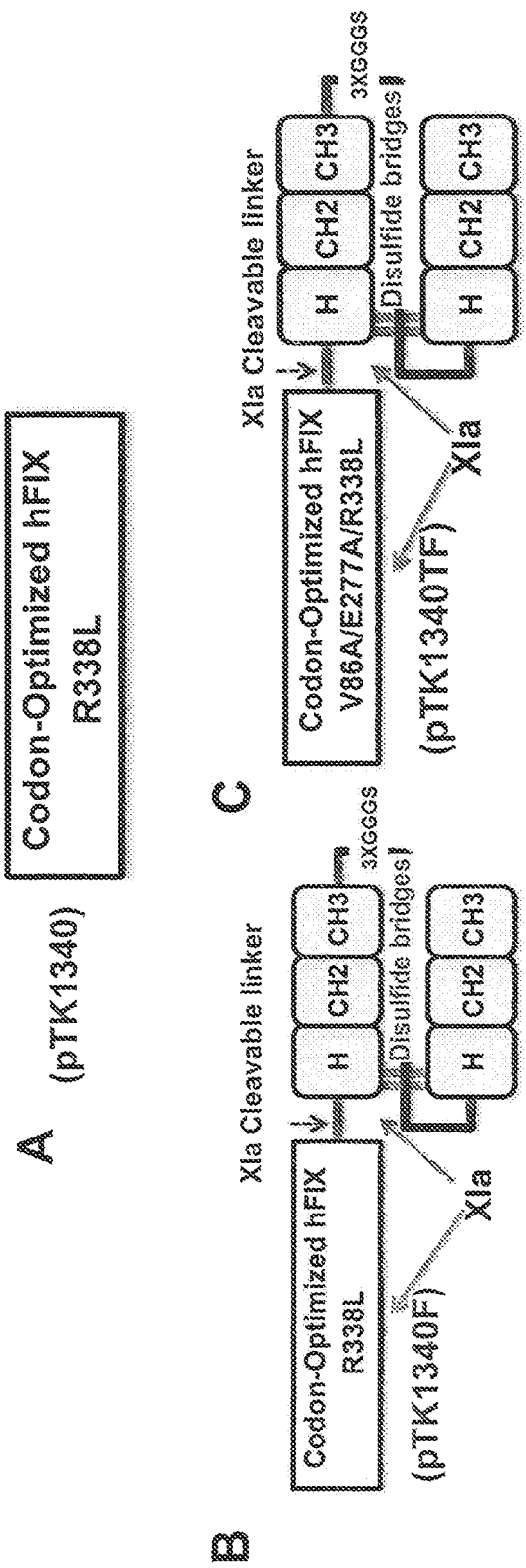
FIGS. 1A-G: Prolongation of hFIX-R338L-2Fc halflife in mouse plasma and Efficient XIa processing in vitro. The structure of the hFIX cDNAs including the hFIX, the XIa cleavable linker, the 3×GGGS linker, the disulfide bridges, and the two Fc-domains. The hinge (H), the CH2 domain and the CH3 domain of the Fc domain are shown. A) The open reading frame of a codon optimized hFIX carrying the R338L mutation. In some embodiments, this cDNA is delivered by the HIV-1 vector pTK1340 (see FIG. 2). B-C) The open reading frames of the disclosed hFIX---2Fc cDNAs encoding a codon optimized hFIX variant containing the R338L mutation (B) or a codon optimized hFIX variant containing the three mutations: V86A, E277A and R338L (C). D-E) The two proteins required to be expressed to establish the desirable hFIX---Fc/Fc monomer (F). G) The undesired byproducts.
Figure 1:
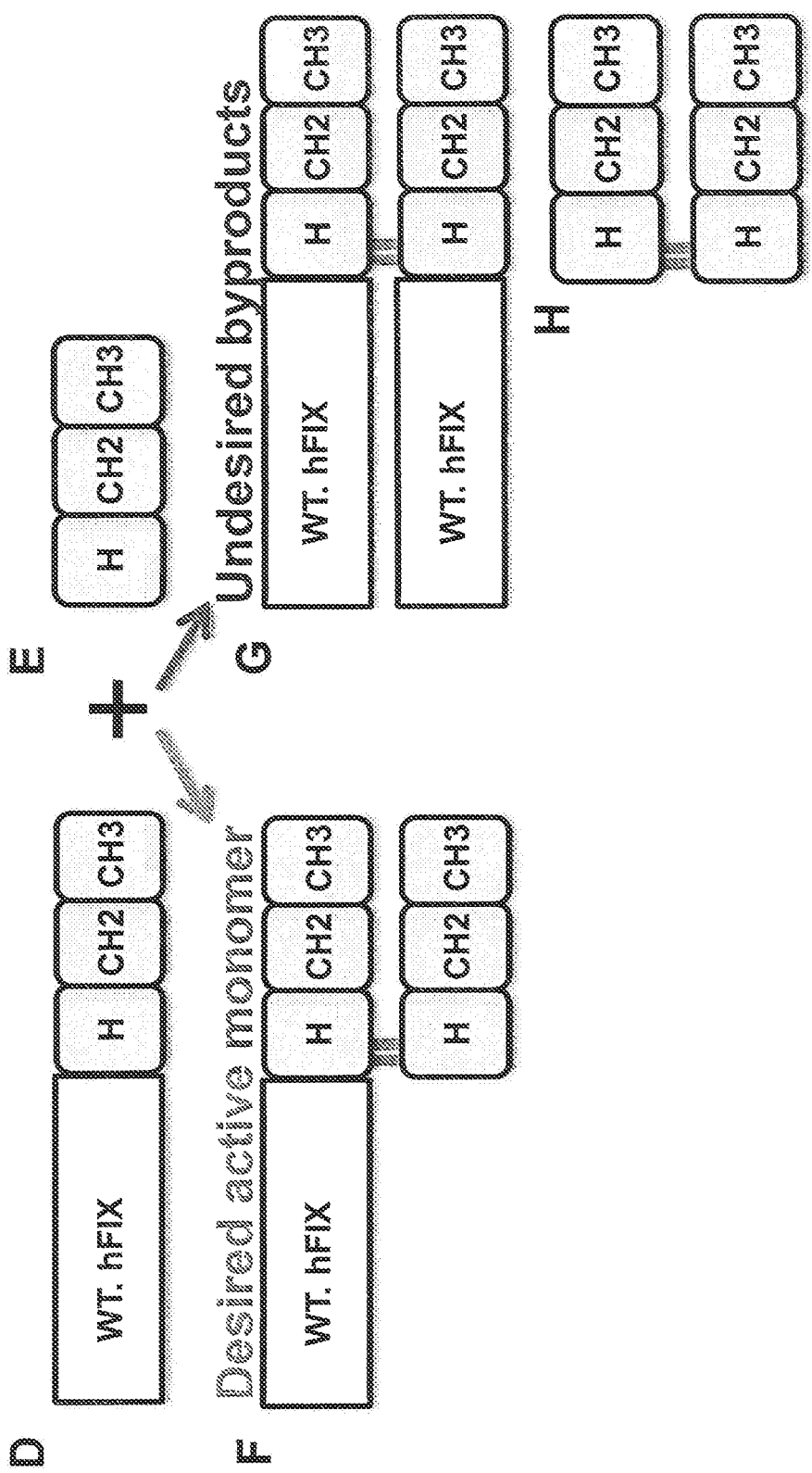

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

The present invention is based on the unexpected discovery of a recombinant Factor IX (FIX) fusion protein that has higher specific activity and a longer useful clotting function relative to wild type or non-modified Factor IX protein. Thus, in one embodiment, the present invention provides a recombinant FIX protein, comprising in the following order (e.g., from amino terminus to carboxy terminus): a) a FIX protein comprising a R338L substitution wherein said amino acid substitution is made at a position in reference to the amino acid sequence of SEQ ID NO:1 (wild type human FIX); b) a first linker sequence comprising a cleavage site; c) a first immunoglobulin (Ig) Fc domain d) a second linker sequence; and e) a second Ig Fc domain, wherein said first Ig Fe domain and said second Ig Fc domain are associated in the FIX fusion protein via one or more disulfide bonds.

In some embodiments, the first and/or second Ig Fc domain can be an $IgG_1$ Fc domain, which in particular embodiments can comprise, consist essentially of or consist of the amino acid sequence:

(SEQ ID NO: 2)
```
  1 DKTHTCPPCP APELLGGPSV FLFPPKPKDT LMISRTPEVT CVVVDVSHED PEVKFNWYVD

61 GVEVHNAKTK PREEQYNSTY RVVSVLTVLH QDWLNGKEYK CKVSNKALPA PIEKTISKAK

121 GQPREPQVYT LPPSRDELTK NQVSLTCLVK GFYPSRLAVE WESNGQPENN YKTTPPVLDS

181 DGSFFLYSKL TVDKSRWQQG NVFSCSVMHE ALHNHYTQKS LSLSPGK
``` or a biologically active or functional fragment of this amino acid sequence.

In some embodiments, the recombinant FIX fusion protein of this invention can further comprise a V86A substitution and/or an E277A substitution, wherein said amino acid substitutions are made at a position in reference to the amino acid sequence of SEQ ID NO:1:

(SEQ ID NO: 1)
```
Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
                100                 105                 110

Glu Gly Tyr Arg Leu Ala Glu Asn Gln Lys Ser Cys Glu Pro Ala Val
            115                 120                 125

Pro Phe Pro Cys Gly Arg Val Ser Val Ser Gln Thr Ser Lys Leu Thr
        130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175
```

```
Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
        210                 215                 220

Thr Gly Val Lys Ile Thr Val Val Ala Gly Glu His Asn Ile Glu Gln
225                 230                 235                 240

Thr Glu His Thr Gln Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Gln Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Gln Val Glu Gly Thr Ser Phe Leu Thr Gly Ile Ile Ser
        370                 375                 380

Trp Gly Glu Gln Cys Ala Met Lys Gly Lys Tyr Gly Ile Tyr Thr Lys
385                 390                 395                 400

Val Ser Arg Tyr Val Asn Trp Ile Lys Gln Lys Thr Lys Leu Thr
                405                 410                 415
```

In some embodiments of this invention, the recombinant FIX fusion protein can be further modified by the addition of extra glycosylation sites to improve the recovery and/or half-life and/or stability of the Factor IX protein. The glycosylation sites may be N-linked glycosylation sites and/or O-linked glycosylation sites.

In some embodiments, the first linker sequence of the recombinant FIX fusion protein of this invention can comprise a XIa cleavage site (e.g., a linker sequence comprising the amino acid sequence: SVSQTSKLTRAETVFPDVDGS, SEQ ID NO:3).

The term "XIa cleavage site" means a site in the amino acid sequence of the FIX fusion protein that is cleaved in the presence of activated Factor XI (FXIa). Nonlimiting examples of other cleavage sites that can be present in the first linker sequence of the FIX fusion protein of this invention include IIa, IXa, VIIa, Xa, XIIa, XIIIa and/or FVIIIa cleavage sites, which would be understood by one of ordinary skill in the art to include the cleavage site recognized by the respective clotting factor when said clotting factor is present in activated form (e.g., the VIIa cleavage site is recognized and cleaved by the activated form of Factor VII (FVIIa).

In some embodiments, the second linker sequence of the recombinant FIX fusion protein of this invention can comprise the amino acid sequence GGGS$_n$ (SEQ ID NO:4), wherein n is any integer (e.g., 1, 2, 3, 4, 5, 6, 7, 8, 9, 10, etc.). In particular embodiments, n is 3. In some embodiments, a second linker sequence of this invention can comprise the amino acid sequence: GSTSGSGKPGSGEGSTKG (SEQ ID NO:5).

In some embodiments, the recombinant FIX fusion protein of this invention can comprise the amino acid sequence:

(SEQ ID NO: 6)
```
  1  MQRVNMIMAE SPGLITICLL GYLLSAECTV FLDHENANKI LNRPKRYNSG KLEEFVQGNL

61  ERECMEEKCS FEEAREVFEN TERTTEFWKQ YVDGDQCESN PCLNGGSCKD DINSYECWCP

121  FQFEGKNCEL DVTCNIKNGR CEQFCKNSAD NKVVCSCTEG YRLAENQKSC EPAVPFPCGR

181  VSVSQTSKLT RAETVFPDVD YVNSTEAETI LDNITQSTQS FNDFTRVVGG EDAKPGQFPW

241  QVVLNGKVDA FCGGSIVNEK WIVTAAHCVE TGVKITVVAG EHNIEETEHT EQKRNVIRII
```

```
301 PHHNYNAAIN KYNHDIALLE LDEPLVLNSY VTPICIADKE YTNIFLKFGS GYVSGWGRVF

361 HKGRSALVLQ YLRVPLVDRA TCLLSTKFTI YNNMFCAGFH EGGRDSCQGD SGGPHVTEVE

421 GTSFLTGIIS WGEECAMKGK YGIYTKVSRY VNWIKEKTKL TSVSQTSKLT RAETVFPDVD

481 GSDKTHTCPP CPAPELLGGP SVFLFPPKPK DTLMISRTPE VTCVVVDVSH EDPEVKFNWY

541 VDGVEVHNAK TKPREEQYNS TYRVVSVLTV LHQDWLNGKE YKCKVSNKAL PAPIEKTISK

601 AKGQPREPQV YTLPPSRDEL TKNQVSLTCL VKGFYPSRLA VEWESNGQPE NNYKTTPPVL

661 DSDGSFFLYS KLTVDKSRWQ QGNVFSCSVM HEALHNHYTQ KSLSLSPGKG GGSGGGSGGG

721 SDKTHTCPPC PAPELLGGPS VFLFPPKPKD TLMISRTPEV TCVVVDVSHE DPEVKFNWYV

781 DGVEVHNAKT KPREEQYNST YRVVSVLTVL HQDWLNGKEY KCKVSNKALP APIEKTISKA

841 KGQPREPQVY TLPPSRDELT KNQVSLTCLV KGFYPSRLAV EWESNGQPEN NYKTTPPVLD

901 SDGSFFLYSK LTVDKSRWQQ GNVFSCSVMH EALHNHYTQK SLSLSPGK*
```

Additionally provided herein is an isolated nucleic acid molecule, comprising, consisting essentially of and/or consisting of a nucleotide sequence encoding the recombinant FIX fusion protein of this invention. Such nucleic acids can be present in a vector, such as an expression cassette. Thus, further embodiments of the invention are directed to expression cassettes designed to express a nucleotide sequence encoding any of the Factor IX fusion proteins of this invention. The nucleic acid molecules, cassettes and or constructs, as well as the vectors of this invention can be present in a cell (e.g., a transformed cell). Thus, various embodiments of the invention are directed to cells containing the vector (e.g., expression cassette). Such a cell can be isolated and/or present in a transgenic animal. Therefore, certain embodiments of the invention are further directed to a transgenic animal comprising a nucleic acid molecule comprising a nucleotide sequence encoding any of the Factor IX fusion proteins of the present invention.

In some embodiments, the nucleic acid molecule of this invention can have a coding sequence that has been optimized relative to a wild type coding sequence (e.g., a coding sequence for FIX) according to protocols well known in the art to, e.g., minimize usage of rare codons (e.g., human codons), remove alternative reading frames, etc., as would be known in the art (e.g., as described in PCT/US2007/071553, the disclosure of which is incorporated herein by reference in its entirety). An optimized nucleic acid molecule of this invention can also be optimized according to known protocols for example, to enhance the activity of a promoter, poly A signal, terminal repeats and/or other elements, as well as to modulate the activity and/or function of cis elements and trans elements involved in gene expression, regulation and/or production, etc., as would be well known in the art.

A nonlimiting example of an optimized nucleic acid molecule of this invention is an isolated nucleic acid molecule comprising the nucleotide sequence:

```
                                                                (SEQ ID NO: 7)
  1   atgcagcgcg tgaacatgat catggccgag agccctggcc tgatcaccat ctgcctgctg 61   ggctacctgc tgagcgccga gtgcaccgtg ttcctggacc acgagaacgc caacaagatc 121   ctgaaccggc caagagata caacagcgg aagctggagg agttcgtgca gggcaacctg 181   gagagggagt gcatggagga gaagtgcagc ttcgaggagg ccagggaagt gttcgagaac 241   accgagcgga ccaccgagtt ctggaagcag tacgtggacg gcgaccagtg cgagagcaac 301   ccttgcctga acggcggcag ctgcaaggac gacatcaaca gctacgagtg ctggtgccct 361   ttcggcttcg agggcaagaa ctgcgagctg gacgtgacct gcaacatcaa gaacggccgc 421   tgcgagcagt tctgcaagaa cagcgccgac aacaaagtgg tgtgtagctg caccgagggc 481   tacagactgg ccgagaacca gaagagctgc gagcccgccg tgcccttccc ctgcggcaga 541   gtgagcgtgt cccagaccag caagctgacc agagccgaga ccgtgttccc cgacgtggac 601   tacgtgaata gcaccgaggc cgagaccatc ctggacaaca tcacccagag cacccagtcc 661   ttcaacgact tcaccagagt gtgggcggc gaggacgcca agcccggcca gttcccctgg 721   caggtggtgc tgaacggcaa agtggatgcc ttctgcggcg gcagcatcgt gaacgagaag 781   tggatcgtga cagccgccca ctgcgtggag accggcgtga agatcaccgt ggtggccggc 841   gaacacaata tcgaggagac cgagcacacc gagcagaagc ggaacgtcat ccggattatc 901   ccccaccaca actacaacgc cgccatcaac aagtacaacc acgacatcgc cctgctggag
```

-continued

```
 961   ctggacgagc ctctggtgct gaatagctac gtgaccccca tctgcatcgc cgacaaggag
1021   tacaccaaca tcttcctgaa gttcggcagc ggctacgtgt ccggctgggg cagagtgttc
1081   cacaagggca gaagcgccct ggtgctgcag tacctgagag tgcccctggt ggacagagcc
1141   acctgcctgt tgagcaccaa gttcaccatc tacaacaaca tgttctgcgc cggcttccac
1201   gagggcggca gagacagctg ccagggcgac agcggcggac cccacgtgac agaggtggaa
1261   ggcaccagct ttctgaccgg catcatcagc tggggcgagg aatgcgccat gaaggggaag
1321   tacggcatct acaccaaggt gtccagatac gtgaactgga tcaaagaaaa gaccaagctg
1381   acatctgtgt ctcagacctc taagctgaca cgggccgaaa ctgtgtttcc tgatgtggac
1441   ggcagcgaca agacccacac ctgtcctcca tgtcccgccc ctgaactgct gggcggacct
1501   agcgtgttcc tgttccccc  aaagcccaag gacaccctga tgatcagccg gaccccgaa
1561   gtgacctgcg tggtggtgga tgtgtcccac gaggaccctg aagtgaagtt caattggtat
1621   gtggatggcg tggaagtgca caacgccaag acaaagccca gagaggaaca gtacaactcc
1681   acctaccggg tggtgtccgt gctgaccgtg ctgcaccagg actggctgaa tggcaaagag
1741   tataagtgca aagtgtccaa caaggccctg cctgccccca tcgagaaaac catcagcaag
1801   gccaagggcc agccccgcga accccaggtg tacacactgc ccctagcag  ggacgagctg
1861   accaagaacc aggtgtccct gacctgtctc gtgaagggct tctaccctag ccggctggcc
1921   gtggaatggg agagcaatgg ccagcccgag aacaattaca agaccacccc ccctgtgctg
1981   gacagcgacg gctcattctt Cctgtacagc aaactgaccg tggacaagag ccggtggcag
2041   cagggcaatg tgttcagctg tagcgtgatg cacgaggccc tgcacaacca ctacacccag
2101   aagtctctga gcctgagccc cggcaagggc ggaggaagtg ggggaggatc tggcggcggc
2161   tccgataaga cacatacctg ccccccttgc cctgcccag  agctgctggg aggcccttct
2221   gtgtttctgt ttccacctaa gcctaaagat acactgatga tctcccgcac acctgaagtg
2281   acatgtgtgg tggtggacgt gtcacatgaa gatccagaag tgaagtttaa ttggtacgtg
2341   gacggggtgg aagtgcataa tgctaagacc aaacccggg  aagaacagta taacagcaca
2401   tacagagtgg tgtctgtgct gacagtgctg catcaggatt ggctgaacgg gaaagaatac
2461   aaatgtaaag tgtctaacaa agctctgccc gctcctatcg aaaagacaat ctccaaggct
2521   aaaggacagc ccagagaacc tcaggtgtac acactgcctc catcccgcga cgagctgaca
2581   aaaaatcagg tgtcactgac atgcctcgtg aagggtttt  atccatctag gctggctgtg
2641   gaatgggaat ccaacggaca gcctgaaaac aactataaga acacacctcc cgtgctggac
2701   tccgatggct cattttttct gtattccaag ctgactgtgg ataagtccag atggcagcag
2761   ggaaacgtgt tctcctgttc tgtgatgcat gaagctctgc ataatcatta tacccagaaa
2821   agcctgtccc tgtcccctgg caagtga
```

The nucleic acid molecule of this invention can be present in a vector, which can be a plasmid vector or a viral vector. Nonlimiting examples of a viral vector of this invention include a retroviral vector, a lentiviral vector, an adenoviral vector, an adeno-associated viral vector, an alphavirus vector, a vaccinia viral vector, a herpesviral vector, etc., as are known in the art.

Furthermore, the vector of this invention can have a vector genome that has been optimized relative to a wild type vector genome, e.g., to enhance the activity of viral cis elements required for replication, packaging and/or delivery, etc., as would be well known in the art. Such an optimized vector can comprise an optimized transcription cassette, optimized terminal repeats, etc., as would be well known in the art.

In some embodiments of this invention, the viral vector can be an integration deficient lentivirus vector (IDLV) or an integration competent lentivirus vector (ICLV). In particular embodiments, the present invention provides an IDLV and an ICLV carrying an expression cassette comprising an internal poly adenylation signal that expresses, as one non-limiting example, 2Fc-hFIX, in the same or in opposite orientation to the long terminal repeats (LTRs) and methods of enhancing production of said IDLVs and ICLVs by rendering the vector producing cells resistant to, or lacking expression of, PKR using either shRNA directed to PKR or mutating the PKR loci (e.g., using gene-editing technology such as Crispr-CAS9 or zinc-finger nucleases and/or Talens) in the producer cell line genome, or by co-expressing viral genes or mRNAs that inhibit PKR activity (e.g., CMV TRS1 protein or adenovirus Va RNA).

In particular embodiments, the present invention provides an IDLV or an ICLV comprising two nucleotide sequences which are in opposite orientation to each other (i.e., complementary). These vectors can either contain, or can be devoid of, an internal expression cassette, which can comprise either a Pol II or Pol III promoter, a cDNA, a shRNA, a microRNA, or any combination thereof. The 3' U3 region in these vectors may comprise the parental HIV-1 3' U3 region, self-inactivating 3'U3, an inducible promoter, and/or a tissue specific promoter, including but not limited to, a hematopoietic stem cell specific, neuronal specific, glial specific, hepatic specific, muscle specific, T cell specific and/or antigen presenting cell (APC) specific promoter.

Additionally, the invention provides methods of enhancing production of the IDLVs and ICLVs of this invention by rendering the vector producing cells resistant to, or lacking expression of, PKR, for example, by using shRNA directed to PKR or by mutating the PKR loci (e.g., using gene-editing technology such as Crispr-CAS9 or zinc-finger nucleases and/or Talens) in the producer cell line genome, and/or by co-expressing viral genes or mRNAs that inhibit PKR activity (e.g., CMV TRS1 protein or adenovirus Va RNA).

Thus, in some embodiments, the present invention provides an RNA-regulated protein kinase (PKR) resistant packaging cell line that generates high titers of gp64– pseudotyped vectors. In particular embodiments, the present invention provides an RNA-regulated protein kinase (PKR) resistant packaging cell line that generates increased titers of gp64– pseudotyped vectors relative to a packaging cell line that is not an RNA-regulated PKR resistant cell line.

In various embodiments, the nucleic acid molecule of this invention can be present in a cell transiently and/or can be stably integrated into the genome of the cell and/or the genome of the cell. The nucleotide sequence can also be stably expressed in the cell even without being integrated into the genome, via a plasmid or other nucleic acid construct as would be well known in the art.

The FIX protein of this invention can be a FIX protein of any species that produces FIX and in particular embodiments is a human FIX protein.

The FIX fusion proteins according to the invention are produced and characterized by methods well known in the art and as described herein. These methods include determination of clotting time (partial thromboplastin time (PPT) assay) and administration of the FIX fusion protein to a test animal to determine recovery, half life, and bioavailability by an appropriate immunoassay and/or activity-assay, as are well known in the art.

The term "subject" as used herein is intended to mean any animal, in particular mammals, such as humans, and may, where appropriate, be used interchangeably with the term "patient."

The term "gene therapy" refers to a method of changing the expression of an endogenous gene by exogenous administration of a gene. As used herein, "gene therapy" also refers to the replacement of a defective gene encoding a defective protein, or replacement of a missing gene, by introducing a functional gene corresponding to the defective or missing gene into somatic or stem cells of an individual in need. Gene therapy can be accomplished by ex vivo methods, in which differentiated or somatic stem cells are removed from the individual's body followed by the introduction of a normal copy of the defective gene into the explanted cells using a viral vector as the gene delivery vehicle. In addition, in vivo direct gene transfer technologies allow for gene transfer into cells in the individual in situ using a broad range of viral vectors, liposomes, protein DNA complexes or naked DNA in order to achieve a therapeutic outcome. The term "gene therapy" also refers to the replacement of a defective gene encoding a defective protein by introducing a polynucleotide that functions substantially the same as the defective gene or protein should function if it were not defective into somatic or stem cells of an individual in need.

In the present invention, gene therapy is employed in the context of administering to a subject a nucleic acid molecule comprising a nucleotide sequence encoding a FIX fusion protein of this invention. Further provided herein is a method of delivering a FIX fusion protein of this invention to a cell, comprising introducing into the cell a nucleic acid molecule comprising a nucleotide sequence encoding the FIX fusion protein under conditions whereby the nucleotide sequence is expressed to produce the FIX fusion protein in the cell. The cell can be a cell that is introduced into a subject and/or the cell can be a cell already present in the subject.

As nonlimiting examples, the following methods can be used to introduce nucleic acid molecules of this invention in various cell types:

1. A nucleic acid vector (e.g., a plasmid vector) encoding the FIX fusion protein can be delivered directly to cells (e.g., mammalian cells) by electroporation.
2. A nucleic acid vector (e.g., a plasmid vector) encoding the FIX fusion protein can be delivered directly to cells by chemical transformation.
3. A viral vector (e.g., a retroviral vector, a lentiviral vector, an adenoviral vector, an adeno associated viral vector, an alphavirus vector, a vaccinia viral vector, a herpesviral vector, etc., as are known in the art) comprising a nucleotide sequence encoding the FIX fusion protein can be used to deliver the FIX fusion protein to cells (e.g., mammalian cells).
4. Lipid mediated delivery (e.g., lipofectamine, oligofectamine) can also be employed for introduction of a nucleic acid molecule encoding the FIX fusion protein into mammalian cells.

In some embodiments, the FIX fusion protein of this invention can be directly introduced in various cell types using a membrane penetrating peptide (e.g., cell penetrating peptide). This can involve fusing the FIX fusion protein with the membrane penetrating peptide.

DEFINITIONS

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount (e.g., an amount of methylation) and the like, is meant to include variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" when used in a claim of this invention is not intended to be interpreted to be equivalent to "comprising."

The term "pharmacokinetic properties" has its usual and customary meaning and refers to the absorption, distribution, metabolism and excretion of the Factor IX protein.

The usual and customary meaning of "bioavailability" is the fraction or amount of an administered dose of a biologically active drug that reaches the systemic circulation. In the context of embodiments of the present invention, the term "bioavailability" includes the usual and customary meaning but, in addition, is taken to have a broader meaning to include the extent to which the Factor IX protein is bioactive. In the case of Factor IX, for example, one measurement of "bioavailability" is the procoagulant activity of Factor IX protein obtained in the circulation post-infusion.

"Posttranslational modification" has its usual and customary meaning and includes but is not limited to removal of leader sequence, γ-carboxylation of glutamic acid residues, β-hydroxylation of aspartic acid residues, N-linked glycosylation of asparagine residues, O-linked glycosylation of serine and/or threonine residues, sulfation of tyrosine residues, phosphorylation of serine residues and any combination thereof.

As used herein, "biological activity" is determined with reference to a standard derived from human plasma. For Factor IX, the standard is MONONINE® (ZLB Behring). The biological activity of the standard is taken to be 100%.

The term "Factor IX protein" or "FIX protein" as used herein includes wild type Factor IX protein as well as naturally occurring or man-made proteins (e.g., the T/A dimorphism in the activation peptide of human FIX at position 148 (numbering based on the mature human FIX amino acid sequence of SEQ ID NO:1, which shows a T at position 148) as described in Graham et al. ("The Malmo polymorphism of coagulation factor IX, an immunologic polymorphism due to dimorphism of residue 148 that is in linkage disequilibrium with two other FIX polymorphisms" *Am. J Hum. Genet.* 42:573-580 (1988)) Thus, in some embodiments, a FIX protein of this invention includes a FIX protein having the amino acid sequence of SEQ ID NO:1, wherein the amino acid at position 148 can be a T or an A and a subject can be either heterozygous or homozygous for either T or A at this site. A FIX protein of this invention can further include mutated forms of FIX as are known in the literature (see, e.g., Chang et al. "Changing residue 338 in human factor IX from arginine to alanine causes an increase in catalytic activity" *J. Biol. Chem.* 273:12089-94 (1998); Cheung et al. "Identification of the endothelial cell binding site for factor IX" *PNAS USA* 93:11068-73 (1996); Horst, *Molecular Pathology,* page 361 (458 pages) CRC Press, 1991, the entire contents of each of which are incorporated by reference herein). A FIX protein of this invention further includes any other naturally occurring human FIX protein or man made human FIX protein now known or later identified, and derivatives and active fragments/active domains thereof, as are known in the art. A Factor IX protein of this invention further includes the pharmacologically active form of FIX, which is the molecule from which the activation peptide has been cleaved out of the protein by the action of proteases (or by engineering it out of the protein by removing it at the nucleic acid level), resulting in two non-contiguous polypeptide chains for FIX (light chain and heavy chain) folded as the functional FIX clotting factor.

The term "half life" or "$t_{1/2}$" is a broad term which includes the usual and customary meaning as well as the usual and customary meaning found in the scientific literature for Factor IX. Specifically included in this definition is a measurement of a parameter associated with Factor IX which defines the time post-infusion for a decrease from an initial value measured at infusion to half the initial value. In some embodiments, the half life of FIX can be measured in blood and/or blood components using an antibody to Factor IX in a variety of immunoassays, as are well known in the art and as described herein. Alternatively, half life may be measured as a decrease in Factor IX activity using functional assays including standard clotting assays, as are well known in the art and as described herein.

The term "recovery" as used herein includes the amount of FIX, as measured by any acceptable method including but not limited to FIX antigen levels or FIX protease or clotting activity levels, detected in the circulation of a recipient animal or human subject at the earliest practical time of removing a biological sample (e.g., a blood or blood product sample) for the purpose of measuring the level of FIX following its infusion, injection, delivery or administration otherwise. With current methodologies, the earliest biological sampling time for measuring FIX recovery typically falls within the first 15 minutes post infusion, injection, or delivery/administration otherwise of the FIX, but it is reasonable to expect quicker sampling times as scientific and/or clinical technologies improve. In essence, the recovery value for FIX is meant here to represent the maximum fraction of infused, injected or otherwise delivered/administered FIX that can be measured in the circulation of the recipient at the earliest possible time point following infusion, injection, or other delivery to a recipient animal or patient.

The term "glycosylation site(s)" is a broad term that has its usual and customary meaning. In the context of the present application the term applies to both sites that potentially could accept a carbohydrate moiety, as well as sites within the protein, specifically FIX, on which a carbohydrate moiety has actually been attached and includes any amino acid sequence that could act as an acceptor for oligosaccharide and/or carbohydrate.

The term "isolated" can refer to a nucleic acid or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

An "isolated cell" refers to a cell that is separated from other cells and/or tissue components with which it is normally associated in its natural state. For example, an isolated cell is a cell that is part of a cell culture. An isolated cell can also be a cell that is administered to or introduced into a subject, e.g., to impart a therapeutic or otherwise beneficial effect.

The Factor IX fusion protein, nucleic acid molecule, vector and/or cell of this invention can be included in a composition with a pharmaceutically acceptable carrier. Some embodiments of this invention are also directed to a kit which includes the Factor IX fusion protein of this invention.

The Factor IX protein of this invention can be used in a method of treating a bleeding disorder by administering to a subject (e.g., a subject in need thereof) an effective amount of the Factor IX fusion protein, nucleic acid molecule, vector, cell and/or composition of this invention.

Also provided herein is a method of increasing the bioavailablity of a Factor IX protein in a subject, comprising administering to a subject (e.g., a subject in need thereof) an effective amount of the Factor IX fusion protein, nucleic acid molecule, vector, cell and/or composition of this invention.

Bleeding disorders that can be treated according to the methods of this invention include a FIX deficiency, hemophilia B and Christmas disease. Such treatment protocols and dosing regimens for administering or delivering Factor IX to a subject in need thereof are well known in the art.

As used herein the term "bleeding disorder" reflects any defect, congenital, acquired or induced, of cellular, physiological, or molecular origin that is manifested in bleedings. Examples are clotting factor deficiencies (e.g., hemophilia A and B or deficiency of coagulation Factors XI or VII), clotting factor inhibitors, defective platelet function, thrombocytopenia, von Willebrand's disease, or bleeding induced by surgery or trauma.

The term "bleeding episode" is meant to include uncontrolled and excessive bleeding. Bleeding episodes may be a major problem both in connection with surgery and other forms of tissue damage. Uncontrolled and excessive bleeding may occur in subjects having a normal coagulation system and subjects having coagulation or bleeding disorders.

Many expression vectors can be used to create genetically engineered cells. Some expression vectors are designed to express large quantities of recombinant proteins after amplification of transfected cells under a variety of conditions that favor selected, high expressing cells, Some expression vectors are designed to express large quantities of recombinant proteins without the need for amplification under selection pressure. The present invention includes the production of genetically engineered cells according to methods standard in the art and is not dependent on the use of any specific expression vector or expression system.

To create a genetically engineered cell to produce large quantities of a Factor IX protein of this invention, cells are transfected with an expression vector that contains the cDNA encoding a target protein (e.g., the FIX fusion protein of this invention). In some embodiments, the target protein is expressed with selected co-transfected enzymes that cause proper post-translational modification of the target protein to occur in a given cell system.

The cell may be selected from a variety of sources, but is otherwise a cell that may be transfected with an expression vector containing a nucleic acid, preferably a cDNA encoding a Factor IX fusion protein.

The practice of the present invention employs, unless otherwise indicated, conventional techniques of molecular biology, microbiology, recombinant DNA, and immunology, which are within the skill of the art. Such techniques are explained fully in the literature. See, e.g., Sambrook, et al., *Molecular Cloning; A Laboratory Manual*, 2nd ed. (1989); *DNA Cloning*, Vols. I and II (D. N Glover, ed. 1985); *Oligonucleotide Synthesis* (M. J. Gait, ed. 1984); *Nucleic Acid Hybridization* (B. D. Hames & S. J. Higgins, eds. 1984); *Transcription and Translation* (B. D. Hames & S. J. Higgins, eds. 1984); *Animal Cell Culture* (R. I. Freshney, ed. 1986); *Immobilized Cells and Enzymes* (IRL Press, 1986); B. Perbal, *A Practical Guide to Molecular Cloning* (1984); the series, *Methods in Enzymology* (Academic Press, Inc.), particularly Vols. 154 and 155 (Wu and Grossman, and Wu, eds., respectively); *Gene Transfer Vectors for Mammalian Cells* (J. H. Miller and M. P. Calos, eds. 1987, Cold Spring Harbor Laboratory); *Immunochemical Methods in Cell and Molecular Biology*, Mayer and Walker, eds. (Academic Press, London, 1987); Scopes, *Protein Purification: Principles and Practice,* 2nd ed. 1987 (Springer-Verlag, N.Y.); and *Handbook of Experimental Immunology* Vols I-IV (D. M. Weir and C. C. Blackwell, eds 1986). All patents, patent applications, and publications cited in the specification are incorporated herein by reference in their entireties.

Genetic Engineering Techniques

The production of cloned genes, recombinant DNA, vectors, transformed host cells, proteins and protein fragments by genetic engineering is well known. See, e.g., U.S. Pat. No. 4,761,371 to Bell et al. at Col. 6, line 3 to Col. 9, line 65; U.S. Pat. No. 4,877,729 to Clark et al. at Col. 4, line 38 to Col. 7, line 6; U.S. Pat. No. 4,912,038 to Schilling at Col. 3, line 26 to Col. 14, line 12; and U.S. Pat. No. 4,879,224 to Wallner at Col. 6, line 8 to Col. 8, line 59.

A vector is a replicable DNA construct. Vectors are used herein either to amplify nucleic acid encoding Factor IX protein and/or to express nucleic acid which encodes Factor IX protein. An expression vector is a replicable nucleic acid construct in which a nucleotide sequence encoding a Factor IX protein is operably linked to suitable control sequences capable of effecting the expression of the nucleotide sequence to produce a Factor IX protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences that control the termination of transcription and translation.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors can contain a promoter and RNA binding sites that are operably linked to the gene to be expressed and are operable in the host organism.

DNA regions or nucleotide sequences are operably linked or operably associated when they are functionally related to each other. For example, a promoter is operably linked to a coding sequence if it controls the transcription of the sequence; or a ribosome binding site is operably linked to a coding sequence if it is positioned so as to permit translation of the sequence.

Transformed host cells are cells which have been transformed, transduced and/or transfected with Factor IX protein vector(s) constructed using recombinant DNA techniques.

Suitable host cells include prokaryote, yeast or higher eukaryotic cells such as mammalian cells and insect cells. Cells derived from multicellular organisms are a particularly suitable host for recombinant Factor IX protein synthesis, and mammalian cells are particularly preferred. Propagation of such cells in cell culture has become a routine procedure (*Tissue Culture*, Academic Press, Kruse and Patterson, editors (1973)). Examples of useful host cell lines are VERO and HeLa cells, Chinese hamster ovary (CHO) cell lines, and WI138, HEK 293, BHK, COS-7, CV, and MDCK cell lines. Expression vectors for such cells ordinarily include (if necessary) an origin of replication, a promoter located upstream from the nucleotide sequence encoding Factor IX protein to be expressed and operatively associated therewith, along with a ribosome binding site, an RNA splice site (if intron-containing genomic DNA is used), a polyadenylation site, and a transcriptional termination sequence. In a preferred embodiment, expression is carried out in Chinese Hamster Ovary (CHO) cells using the expression system of U.S. Pat. No. 5,888,809, which is incorporated herein by reference in its entirety.

The transcriptional and translational control sequences in expression vectors to be used in transforming vertebrate cells are often provided by viral sources. For example, commonly used promoters are derived from polyoma, Adenovirus 2, and Simian Virus 40 (SV40). See. e.g., U.S. Pat. No. 4,599,308.

An origin of replication may be provided either by construction of the vector to include an exogenous origin, such as may be derived from SV 40 or other viral (e.g., polyoma, adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the nucleic acid encoding the Factor IX protein. Examples of suitable selectable markers are dihydrofolate reductase (DHFR) or thymidine kinase. This method is further described in U.S. Pat. No. 4,399,216 which is incorporated by reference herein in its entirety.

Other methods suitable for adaptation to the synthesis of Factor IX protein in recombinant vertebrate cell culture include those described in Gething et al. *Nature* 293:620 (1981); Mantei et al. *Nature* 281:40; and Levinson et al., EPO Application Nos. 117,060A and 117,058A, the entire contents of each of which are incorporated herein by reference.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the nucleotide sequence to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example *Escherichia coli* (*E. coli*) or bacilli. Higher eukaryotic cells include established cell lines of mammalian origin as described below. Exemplary host cells are *E. coli* W3110 (ATCC 27,325), *E. coli* B, *E. coli* X1776 (ATCC 31,537) and *E. coli* 294 (ATCC 31,446). A broad variety of suitable prokaryotic and microbial vectors are available. *E. coli* is typically transformed using pBR322. Promoters most commonly used in recombinant microbial expression vectors include the betalactamase (penicillinase) and lactose promoter systems (Chang et al. *Nature* 275:615 (1978); and Goeddel et al. *Nature* 281:544 (1979)), a tryptophan (trp) promoter system (Goeddel et al. *Nucleic Acids Res.* 8:4057 (1980) and EPO App. Publ. No. 36,776) and the tac promoter (De Boer et al. *Proc. Natl. Acad. Sci.* USA 80:21 (1983)). The promoter and Shine-Dalgarno sequence (for prokaryotic host expression) are operably linked to the nucleic acid encoding the Factor IX protein, i.e., they are positioned so as to promote transcription of Factor IX messenger RNA from DNA.

Eukaryotic microbes such as yeast cultures may also be transformed with protein-encoding vectors (see, e.g., U.S. Pat. No. 4,745,057). *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, nucleic acid encoding Factor IX protein, sequences for polyadenylation and transcription termination, and a selection gene. An exemplary plasmid is YRp7, (Stinchcomb et al. *Nature* 282:39 (1979); Kingsman et al. *Gene* 7:141 (1979); Tschemper et al. *Gene* 10:157 (1980)). Suitable promoting sequences in yeast vectors include the promoters for metallothionein, 3-phosphoglycerate kinase (Hitzeman et al. *J. Biol. Chem.* 255:2073 (1980) or other glycolytic enzymes (Hess et al. *J. Adv. Enzyme Reg.* 7:149 (1968); and Holland et al. *Biochemistry* 17:4900 (1978)). Suitable vectors and promoters for use in yeast expression are further described in R. Hitzeman et al., EPO Pubin. No. 73,657.

Cloned coding sequences of the present invention may encode FIX of any species of origin, including mouse, rat, dog, opossum, rabbit, cat, pig, horse, sheep, cow, guinea pig, platypus, and human, but preferably encode Factor IX protein of human origin. Nucleic acid encoding Factor IX that is hybridizable with nucleic acid encoding proteins disclosed herein is also encompassed. Hybridization of such sequences may be carried out under conditions of reduced stringency or even stringent conditions (e.g., stringent conditions as represented by a wash stringency of 0.3M NaCl, 0.03M sodium citrate, 0.1% SDS at 60° C. or even 70° C.) to nucleic acid encoding Factor IX protein disclosed herein in a standard in situ hybridization assay. See, e.g., Sambrook et al., *Molecular Cloning, A Laboratory Manual* (2d Ed. 1989) Cold Spring Harbor Laboratory).

The FIX proteins produced according to the invention may be expressed in transgenic animals by known methods. See for example, U.S. Pat. No. 6,344,596, which is incorporated herein by reference in its entirety. In brief, transgenic animals may include but are not limited to farm animals (e.g., pigs, goats, sheep, cows, horses, rabbits and the like) rodents (such as mice, rats and guinea pigs), and domestic pets (for example, cats and dogs). Livestock animals such as pigs, sheep, goats and cows, are particularly preferred in some embodiments.

The transgenic animal of this invention is produced by introducing into a single cell embryo an appropriate polynucleotide that encodes a human Factor IX protein of this invention in a manner such that the polynucleotide is stably integrated into the DNA of genii line cells of the mature animal, and is inherited in normal Mendelian fashion. The transgenic animal of this invention would have a phenotype of producing the FIX protein in body fluids and/or tissues. The FIX protein would be removed from these fluids and/or tissues and processed, for example for therapeutic use. (See, e.g., Clark et al. "Expression of human anti-hemophilic factor IX in the milk of transgenic sheep" *Bio/Technology* 7:487-492 (1989); Van Cott et al. "Haemophilic factors produced by transgenic livestock: abundance can enable alternative therapies worldwide" *Haemophilia* 10(4):70-77 (2004), the entire contents of which are incorporated by reference herein).

DNA molecules can be introduced into embryos by a variety of means including but not limited to microinjection, calcium phosphate mediated precipitation, liposome fusion, or retroviral infection of totipotent or pluripotent stem cells. The transformed cells can then be introduced into embryos and incorporated therein to form transgenic animals. Methods of making transgenic animals are described, for example, in *Transgenic Animal Generation and Use* by L. M. Houdebine, Harwood Academic Press, 1997. Transgenic animals also can be generated using methods of nuclear transfer or cloning using embryonic or adult cell lines as described for example in Campbell et al., *Nature* 380:64-66 (1996) and Wilmut et al., *Nature* 385:810-813 (1997). Further a technique utilizing cytoplasmic injection of DNA can be used as described in U.S. Pat. No. 5,523,222.

Factor IX-producing transgenic animals can be obtained by introducing a chimeric construct comprising Factor IX-encoding sequences. Methods for obtaining transgenic animals are well-known. See, for example, Hogan et al., *MANIPULATING THE MOUSE EMBRYO*, (Cold Spring Harbor Press 1986); Krimpenfort et al., *Bio/Technology* 9:88 (1991); Palmiter et al., Cell 41:343 (1985), Kraemer et al., *GENETIC MANIPULATION OF THE EARLY MAMMALIAN EMBRYO*, (Cold Spring Harbor Laboratory Press 1985); Hammer et al., *Nature* 315:680 (1985); Wagner et al., U.S. Pat. No. 5,175,385; Krimpenfort et al., U.S. Pat. No. 5,175,384, Janne et al., *Ann. Med.* 24:273 (1992), Brem et al., *Chim. Oggi.* 11:21 (1993), Clark et al., U.S. Pat. No. 5,476,995, all incorporated by reference herein in their entireties.

In some embodiments, cis-acting regulatory regions may be used that are "active" in mammary tissue in that the promoters are more active in mammary tissue than in other tissues under physiological conditions where milk is synthesized. Such promoters include but are not limited to the short and long whey acidic protein (WAP), short and long α, β and κ casein, α-lactalbumin and β-lactoglobulin ("BLG") promoters. Signal sequences can also be used in accordance with this invention that direct the secretion of expressed proteins into other body fluids, particularly blood and urine. Examples of such sequences include the signal peptides of secreted coagulation factors including signal peptides of Factor IX, protein C, and tissue-type plasminogen activator.

Among the useful sequences that regulate transcription, in addition to the promoters discussed above, are enhancers, splice signals, transcription termination signals, polyadenylation sites, buffering sequences, RNA processing sequences and other sequences which regulate the expression of transgenes.

Preferably, the expression system or construct includes a 3' untranslated region downstream of the nucleotide sequence encoding the desired recombinant protein. This region can increase expression of the transgene. Among the 3' untranslated regions useful in this regard are sequences that provide a poly A signal.

Suitable heterologous 3'-untranslated sequences can be derived, for example, from the SV40 small t antigen, the casein 3' untranslated region, or other 3' untranslated sequences well known in this art. Ribosome binding sites are also important in increasing the efficiency of expression of FIX. Likewise, sequences that regulate the post-translational modification of FIX are useful in the invention.

Factor IX coding sequences, along with vectors and host cells for the expression thereof, are disclosed in European Patent App. 373012, European Patent App. 251874, PCT Patent Appl. 8505376, PCT Patent Appln. 8505125, European Patent Appln. 162782, and PCT Patent Appln. 8400560, all of which are incorporated by reference herein in their entireties.

EXAMPLES

Example 1. Combining Multiple Modifications in hFIX cDNA to Facilitate Intramolecular Interactions within a Tandem 2 Fe-Domains to Efficiently Extend the Half-Life and to Maintain Enhanced Specific Activity of hFIX Variants Encoded by Codon-Optimized Human Factor IX The invention is based on the discovery that combining several modifications in the human factor IX (hFIX) cDNA will yield a highly efficacious cDNA suitable for human clinical and significantly more clinically potent than hFIX cDNAs carrying only some of the modifications described herein.

Figure 2:
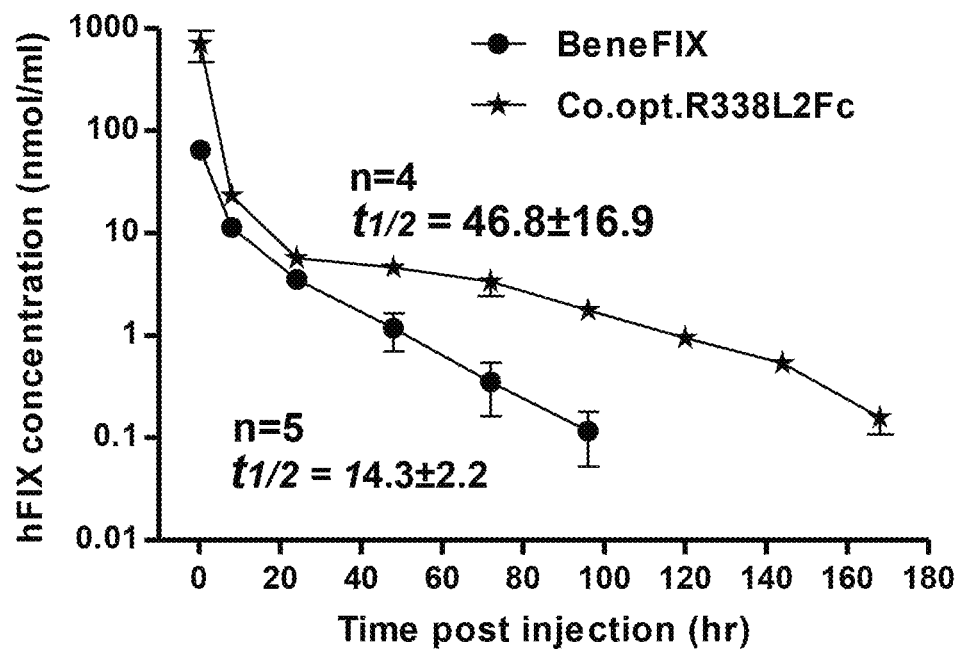
FIG. 2. Pharmacodynamics of BeneFix and R338L-2Fc concentration in hemophilia B mice plasma. The above proteins were intravenously administrated. Note that at 24 hrs (end of the early phase) post injection plasma concentration of the BeneFix® protein and the R338L-2Fc were comparable. The $t_{1/2}$ of the above proteins between 24 and 96 hrs post injection is indicated.
Figure 3:
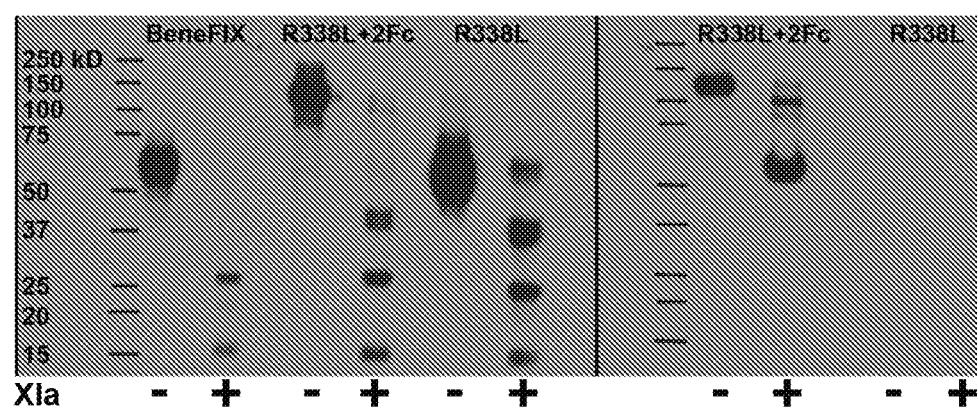
FIG. 3. Western blot analysis showing cleavage by XIa. Conditioned media containing either hFIX R338L or hFIX R338L+2Fc from 293T cells transduced with either pTK1335 or pTK1775 were either treated or not with XIa. Commercially available purified hFIX (BeneFix®) served as positive control. Treated samples were analyzed by western blot analysis using either peroxidase conjugated sheep anti hFIX (left panel) or goat anti rabbit IgG (cross reactive with human IgG). Only low levels of partial XIa cleavage of media derived unpurified hFIX could be observed.
Figure 4:
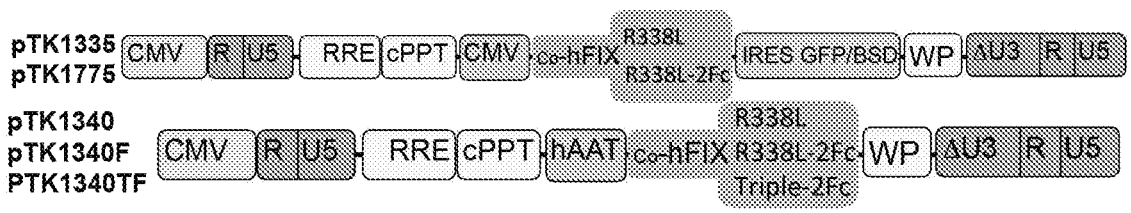
FIG. 4. Physical map of lentiviral vectors carrying the novel modified hFIX cDNAs. The cDNAs of the codon-optimized optimized (co-) hFIX including the co-R338L (pTK1355, pTK1340), co-R338L-Fc (pTK1775, pTK1340F) and the triple mutation V86A/E277A/R338L-2Fc (pTK1340TF) are shown. The CMV and the hAAT promoters are shown. The IRES and the GFP-blasticidin fusion are shown. The lentiviral vectors pTK1335 and pTK1775 efficiently transduced 293T cells line as a means to rapidly generate stable cell line producing hFIX R338L and R338L'-2Fc.

As shown in FIGS. 1B-C, the invention is premised on fusing two human IgG1 Fc domains in-frame to a codon open optimized reading frame (ORF) encoding variants of highly active human factor IX (hFIX) as a means to extend the above proteins' half-life in vivo (see FIG. 2). A linker (preferably but not only) comprising 12 amino acids (3×GGGS) separates the two Fe-domains as a means to facilitate their interaction by disulfide bonds (an intramolecular interaction). This approach is premised on the notion that binding of IgG1 to neonatal Fc receptors (FcRn) redirects it away from lysosomal degradation, back to the cell membrane and into the circulation. Association of two FC-domains by disulfide bonds is required for efficient interaction with the FcRn. Incorporating two Fc domains into a single molecule facilitates their interaction by intramolecular disulfide bonds. A linker encoding a cleavage target sequence for activated factor XI (XIa) is incorporated between the hFIX and the Fc-domains. This allows XIa-mediated dissociation of the hFIX from the 2Fc-domains and maximizes hFIX protein specific activity (see FIG. 3). Codon optimization of the novel cDNA will increase its mRNA stability and enhance its translation, thus rendering expression cassettes carrying the aforementioned hFIX more potent (see FIG. 1) Specific point mutations and their combinations will increase in the specific activity of the novel hFIX protein (FIGS. 1 and 4). Although each of the above modifications improves hFIX function it is their combination that renders the novel hFIX cDNA its superior function for treating hemophilia B patients either by protein replacement therapy or by gene therapy/delivery regimens.

The novel hFIX cDNA prolong hFIX protein half-life in vivo and exhibit high specific activity. Furthermore, its design supports efficient in vivo delivery by viral vectors and facilitates rapid establishment of hFIX producing cell lines. The novel hFIX cDNA comprises several modifications whose combination renders it superior to all currently used hFIX cDNAs.

Earlier protein-replacement studies (preclinical and clinical) reported on an up to 5-fold increase in $t_{1/2}$ of plasma recombinant hFIX-Fc (single domain) monomers. The injected monomer comprised two proteins, an hFIX Fc-domain fusion molecule that was associated via intermolecular disulfide bonds with a free Fc-domain (FIGS. 1 D-G). This system is different and significantly inferior to the disclosed single-protein hFIX-2Fc system in which intramolecular disulfide bonds are readily established between two Fc-domains contained in a single protein.

High Specific Activity.

The above hFIX-Fc fusion exhibits significantly lower specific activity than the native hFIX. Per contra the specific activity of the disclosed hFIX-2Fc cDNAs is comparable or higher than the specific activity of the R338L hFIX variant which is 8-15 fold higher than the specific activity of the native hFIX. Two mechanisms enhance the specific activity of the disclosed hFIX-2Fc protein. A) The novel hFIX-2Fc protein contains the R338L point mutation either alone or in combination with additional two point mutations V86A/E277A (FIGS. 1 and 4). B) In contrast to the hFIX-Fe, a linker encoding a cleavage target sequence for activated factor XI (XIa) is incorporated between the hFIX and the 2Fc-domains. This protein design allows XIa-mediated dissociation of the hFIX from the 2Fcdomains and thus alleviates potential inhibition of hFIX activity by the Fe-domains (FIGS. 1 and 2).

Lack of Inactive Byproducts.

The production of the hFIX-Fc monomer is premised on the establishment of intermolecular bi-sulfide bonds between two proteins (a hFIXFc fusion, and a free Fe-domain) synthesized in the same cell, which also contains significant amounts of undesired byproducts including the less active dimer hFIXFc/hFIX-Fc and the non-active dimer Fc-domain/Fc-domain (FIGS. 1D-G). Per contra, in the disclosed hFIX-2Fc protein, intramolecular disulfide bonds are efficiently established between two Fc-domains (separated by a 12 amino acids (3×GGGS) linker). The aforementioned protein design facilitates efficient folding of the above 2Fc-domains without generating inactive byproducts and thus bestows the disclosed hFIX-2Fc protein with major advantages over the earlier described hFIX-Fc protein (FIGS. 1B-C).

These advantages include:

a) Efficient In Vivo Delivery and Function.

The disclosed hFIX-2Fc protein is expressed from a single expression cassette, which can be efficiently delivered by a single viral vector to target organs in vivo (FIG. 4). Per contra the earlier hFIX-Fc system is premised on two expression cassettes, which can be delivered by either two vectors or by a single vector carrying a bicistronic expression system or a self-cleaving protein sequence. However, the low likelihood of two viral vectors transducing the same cell in equal stoichiometry renders the usage of two viral vectors as a means to deliver the hFIX-Fc to live animals not feasible.

b) A Single Active Protein.

The single hFIX-2Fc protein is highly active and does not have to be purified out from undesirable by products and thus can be efficiently employed in gene replacement therapy applications. Furthermore, the disclosed hFIX-2Fc protein-design, facilitate the establishment of protein producing cell lines for protein replacement therapy. Specifically, the fact that optimal function of the hFIX-2Fc protein does not require intermolecular interaction with additional Fc domains facilitate isolation, and identification of cell clones expressing high level of functional hFIX-2Fc (FIGS. 1 and 4). Per contra the hFIX-Fc/Fc monomer has to be separated from byproducts (the hFIX-Fc dimer (hFIX-Fc/hFIX-Fc) and from the free Fc dimers (Fc/Fc)) (FIG. 1). The fact that the separation/purification of the hFIX-Fc from the above byproducts cannot be done in vivo renders the earlier hFIX-Fc protein not suitable for gene therapy applications. Furthermore the establishment of hFIX-Fc cell lines is significantly complicated by the need to introduce additional expression cassette (expressing the Fc domain) into hFIX-Fc expressing cells and to screen for specific cell clones maintaining the optimal hFIX-Fc/Fc stoichiometry.

The disclosed hFIX-2Fc can be employed in gene replacement (gene therapy) and protein replacement application to treat hemophilia B patients. The increased size of the novel hFIX-2Fc coding sequence may reduce the efficiency of packaging vector mRNA into viral particles. Determining vector transducing units (IU) titers will allow adjustment of vector dose to IU-based titers.

Example 2. A Tandem Fe-Domain as a Means to Extend the $t_{1/2}$ of Circulating Proteins Delivered by Viral Vectors Our laboratory recently published a report demonstrating the ability of integration defective lentiviral vectors (IDLVs) to cure hemophilia B in preclinical settings, providing additional proof of their therapeutic potential. However, further improvements of the IDLV gene delivery system are required in order to establish IDLVs as a therapeutic modality for nonfatal human diseases such as hemophilia B. Thus, we propose: a) to employ a novel PPT-deleted vector to further reduce the low risk of insertional mutagenesis associated with systemic administration of IDLVs, b) to develop and test a novel IDLV-based human factor IX (hFIX) expression cassette as a means to minimize IDLY vector load required to fully correct FIX deficiency in hemophilia B mice, and c) to establish a novel packaging cell line to facilitate production of mobilization resistant IDLVs carrying expression cassettes in opposite orientation to the vector's LTRs. We will focus on characterizing the ability of novel PPT-deleted IDLVs with reduced illegitimate integration to mediate efficient hepatic gene delivery in vivo. We will focus on the development and testing of a novel hFIX cDNA with prolonged in vivo half-life ($t_{1/2}$) and enhanced specific activity using IDLVs for hepatic gene delivery. The efficacy of the new IDLVs to correct FIX deficiency will be tested in hemophilia B mice. We will establish a novel RNA-regulated protein kinase (PKR) resistant packaging cell line that generates high titers of gp64– pseudotyped vectors. A PPT-deletion will render the cell line-generated IDLVs less likely to illegitimately integrate, and internal expression cassettes incorporated in opposite orientation to the LTRs will render them less likely to be mobilized. Overall the described therapeutic approach will yield a highly efficient and significantly safer gene delivery system most suitable for gene replacement therapy of nonfatal human diseases.

Specifically, we will focus our efforts on enhancing the effectiveness of gene and protein replacement therapy using, for example, IDLVs, in correcting FIX deficiency in vivo on two levels: a) we will develop a highly efficacious hFIX cDNA comprising three point mutations (FIX-V86A/E277A/R338L) that significantly increase FIX specific activity in vivo. To increase FIX production per vector genome, the modified hFIX will be codon-optimized; and b) as a means to extend its half-life ($t_{1/2}$) in mouse plasma, two IgG1 Fc-domains separated by a linker will be fused to the C-terminus of the modified hFIX. To preserve hFIX specific activity, a cleavable linker will separate the Fc-domains from the hFIX protein and we will generate IDLVs carrying three co-hFIX cDNAs, including the R338L, the R338L-Fc, and the triple-mutant-Fc. The aforementioned IDLVs will be pseudotyped with the gp64 envelope protein, which has proven highly efficacious for hepatic gene delivery. The above vectors will be administered to hemophilia B mice. We will periodically determine hFIX protein levels and activity in treated mouse plasma, as well as the emergence of vector/transgene-directed immune responses. We will characterize vector biodistribution and determine the therapeutic/genotoxic index (TGI), reflecting the ratio of the percent increase in hFIX activity to vector copy number.

Earlier protein-replacement studies (preclinical and clinical) reported on an up to 5-fold increase in $t_{1/2}$ of plasma recombinant hFIX-Fc monomers. The injected monomer was comprised of two proteins, an hFIX Fc domain fusion molecule that was associated via disulfide bonds with a free Fc-domain. However, the activity of the hFIX-Fc fusion was significantly lower than the activity of the native hFIX. Furthermore, less active and non-active dimer (hFIX-Fc/hFIX-Fc and Fc/FcR, respectively) byproducts were generated in addition to the hFIX-Fc/Fc monomer, which had to be purified. Clearly, in vivo delivery of a two-expression cassette system would not be efficient. Per contra, as shown in FIG. 1, the hFIX-2×Fc cDNA of the present invention was efficiently incorporated into the lentiviral vector system and its translated protein was efficiently processed by XIa and exhibited specific activity (1144.3 IU/mg) comparable to the specific activity of the co-R338L (1170.0 IU/mg) and 8-fold higher than the native hFIX. The novel 2×Fc-fusion approach will pave the way to extend the in vivo $t_{1/2}$ of hFIX and various secreted proteins delivered by viral vectors (including hFVIII), and will simplify the purification of highly active monomers. We have purified the novel R338L-2Fc hFIX and demonstrated that its concentration in hemophilia B mouse plasma declined in the expected biphasic curve. As shown in FIG. 2, at 24 hrs post injection (the end of the early α-phase) plasma concentration of the hFIX R338L-2Fc protein was comparable to that of BeneFix (the most prescribed recombinant factor IX treatment for hemophilia B). However, we could not detect the BeneFix protein later than 96 hrs post injection. Per contra, the R338L-2Fc hFIX protein was readily detected at 168 hrs post injection and its $t_{1/2}$ (between 24 and 96 hrs post injection) was more than 3-fold longer than that of BeneFix (comparable to rFIXFc reported in [18]). Note that the additional two point mutations in hFIX (V86A/E277A/R338L-2Fc) would further increase its specific activity by 2-3 fold (a total of 10-15-fold higher than the wild type hFIX). This modified hFIX will facilitate a single-dose protein therapy once every 2 weeks instead of the current therapeutic regimen of two to three injections of hFIX protein per week. Furthermore, this modified hFIX will significantly reduce the amount of vector required to achieve therapeutic benefits in gene therapy-based protocols.

Our overall goal is to reduce the genotoxic insult associated with IDLV-based therapeutic regimens for hemophilia B, to a point that renders the risk/benefit of these regimens suitable for non-fatal human diseases. Thus, we propose to enhance IDLV delivered hFIX activity as a means to reduce the IDLV load required to correct FIX deficiency. This approach will be based on the codon-optimized (co-) R338L hFIX cDNA, which in an earlier study increased overall hFIX per vector genome by more than 40-fold.

Here we propose two mechanistically independent, yet synergistic strategies to further increase the efficacy of IDLV-delivered hFIX cDNA. The first strategy is premised on a study showing that a hFIX protein comprising the three-mutations V86A/E277A/R338L is significantly more active than the R338L hFIX protein. In this earlier study, the triple mutation-containing hFIX cDNAs were not codon-optimized. We assert that a codon-optimized triple mutant hFIX cDNA as described herein will be more efficacious than the hFIX variant cDNA described previously. The second strategy is directed to fusing 2×Fc-domains to co-hFIX comprising the above triple-mutation as a means to extend its plasma $t_{1/2}$. Our preliminary results (FIG. 1) demonstrate that the specific activity of a recently developed R338L-2×Fc (comprising a cleavable linker) is comparable to that of R338L hFIX, which is more than 10-fold higher than the specific activity of WT hFIX. Per contra the specific activity of hFIX-Fc was significantly lower than that of the WT hFIX.

The proposed studies will be premised on IDLVs carrying three different hFIX cDNAs under the control of a liver specific promoter. These include codon-optimized (co-) R338L, co-R338L-2×Fc, and co-TripleMut-2×Fc (pTK1340, pTK1340F, and pTK1340TF, respectively (FIG. 1)). The vector will be pseudotyped with the gp64 envelope protein and generated by transient three-plasmid transfection. Three doses of each vector (a total of 150, 50, and 15 μg p24gag) will be administered intraperitoneally to hemophilia B mice. Based on our previous studies, we expect that 150 μg of pTK1340 will correct FIX deficiency in the above mice. This study comprises a total of 9 treatment groups (of 10 mice each) and one PBS-injected control group and will be conducted twice. Groups A, B, and C will be treated with pTK1340 (15, 50 and 150μ p24gag, respectively). Groups D, E, and F will be treated with pTK1340F (15, 50 and 150μ p24gag, respectively). Groups G, H, and I will be treated with pTK1340TF (15, 50 and 150μ p24gag, respectively). Group J will be treated with PBS. Mouse plasma will be collected prior to vector administration and at days 7, 14, 21, 28, 60, 120, and 180 post injection. hFIX ELISA and aPTT will be used to determine the concentration and activity of hFIX in mouse plasma. Levels of alanine aminotransferase (ALT) will be determined and employed as a surrogate marker for potential liver damage. Bethesda assays will be employed to monitor for the development of inhibitory antibodies. Mice will be sacrificed at day 180 post injection and DNA will be extracted from various tissues, including liver, heart, brain, kidney, lung, and bone marrow. Gross morphology of the tissues will be evaluated for tumor development. Total and integrating vector copy number will be determined by qPCR and S1/B1-qPCR assay, respectively. The therapeutic/genotoxic index (TGI), reflecting the ratio of % hFIX activity per integrated vector genome in mouse liver will be determined.

Statistical considerations: Appropriate descriptive statistics pertinent to the variables being measured will be calculated. Medians along with the minimum, 25th and 75th percentiles, and maximums will be reported, as well as means along with their respective 95% confidence intervals. Interest lies in comparing groups in a pairwise manner. A method known as "response features analysis" will be used to analyze repeated measures of hFIX (57 earlier grant). This method allows for the comparison of individual profiles using "summary measures." The summary measure that will be used is the AUC (Area Under the Curve). Once the AUCs have been calculated for each animal, the Wilcoxon two-group method will be used to test for differences between these pairwise group comparisons of interest. Since these experiments are exploratory, reported pvalues will be "nominal," or unadjusted for multiple testing.

We expect that due to the extended $t_{1/2}$ of hFIX-2×Fc, correction of factor FIX deficiency in hemophilia B mice using pTK1340F will be achieved with significantly lower vector doses (~4-fold lower) as compared with pTK1340 carrying the parental R338L. Further reduction (~3-fold lower) in IDLV doses required for correcting FIX deficiency would be achieved by using pTK1340TF carrying the triple mutant hFIX fused to 2×Fc. We anticipate that the above IDLVs will exhibit comparable levels of illegitimate integration. Consequently the therapeutic/genotoxic index (TGI) of non-integrating pTK1340TF will be more than 10-fold higher than the TGI of pTK1340. We will generate a PPT-deleted version of pTK1340TF which will exhibit lower levels (~3-fold) of illegitimate integration, resulting in an enhanced TGI that is more than 30-fold higher than the TGI of pTK1340, and thus over 350-fold higher than the TGI of currently used ICLVs. Alternatively, as a means to extend the plasma $t_{1/2}$ of vector-delivered FIX we will replace the 2×Fc-domains with the human albumin coding sequence.

It will be understood by those of skill in the art that numerous and various modifications can be made without departing from the spirit of the present invention. Therefore, it should be clearly understood that the forms of the present invention are illustrative only and are not intended to limit the scope of the present invention.

All publications, patent applications, patents, patent publications, sequences identified by GenBank® database accession numbers and other references cited herein are incorporated by reference in their entireties for the teachings relevant to the sentence and/or paragraph in which the reference is presented.

The invention is defined by the following claims, with equivalents of the claims to be included therein.

```
Fc domain prot → List
Protein sequence 228 aa
                                                              (SEQ ID NO: 2)
   1    DKTHTCPPCP APELLGGPSV FLFPPKPKDT LMISRTPEVT CVVVDVSHED PEVKFNWYVD   60

61    GVEVHNAKTK PREEQYNSTY RVVSVLTVLH QDWLNGKEYK CKVSNKALPA PIEKTISKAK  120

121    GQPREPQVYT LPPSRDELTK NQVSLTCLVK GFYPSRLAVE WESNGQPENN YKTTPPVLDS  180

181    DGSFFLYSKL TVDKSRWQQG NVFSCSVMHE ALHNHYTQKS LSLSPGK*              228

XIa target linker in our FIC-2Fc → List
Protein sequence 21 aa
                                                              (SEQ ID NO: 3)
   1    SVSQTSKLTR AETVFPDVDG S                                            21

ORf hFIX 2Fc in pTK1774 → List
Protein sequence 949 aa
                                                              (SEQ ID NO: 6)
   1    MQRVNMIMAE SPGLITICLL GYLLSAECTV FLDHENANKI LNRPKRYNSG KLEEFVQGNL   60

61    ERECMEEKCS FEEAREVFEN TERTTEFWKQ YVDGDQCESN PCLNGGSCKD DINSYECWCP  120

121    FGFEGKNCEL DVTCNIKNGR CEQFCKNSAD NKVVCSCTEG YRLAENQKSC EPAVPFPCGR  180

181    VSVSQTSKLT RAETVFPDVD YVNSTEAETI LDNITQSTQS FNDFTRVVGG EDAKPGQFPW  240

241    QVVLNGKVDA FCGGSIVNEK WIVTAAHCVE TGVKITVVAG EHNIEETEHT EQKRNVIRII  300

301    PHHNYNAAIN KYNHDIALLE LDEPLVLNSY VTPICIADKE YTNIFLKFGS GYVSGWGRVF  360

361    HKGRSALVLQ YLRVPLVDRA TCLLSTKFTI YNNMFCAGFH EGGRDSCQGD SGGPHVTEVE  420

421    GTSFLTGIIS WGEECAMKGK YGIYTKVSRY VNWIKEKTKL TSVSQTSKLT RAETVFPDVD  480

481    GSDKTHTCPP CPAPELLGGP SVFLFPPKPK DTLMISRTPE VTCVVVDVSH EDPEVKFNWY  540

541    VDGVEVHNAK TKPREEQYNS TYRVVSVLTV LHQDWLNGKE YKCKVSNKAL PAPIEKTISK  600

601    AKGQPREPQV YTLPPSRDEL TKNQVSLTCL VKGFYPSRLA VEWESNGQPE NNYKTTPPVL  660

661    DSDGSFFLYS KLTVDKSRWQ QGNVFSCSVM HEALHNHYTQ KSLSLSPGKG GSGGGSGGG   720

721    SDKTHTCPPC PAPELLGGPS VFLFPPKPKD TLMISRTPEV TCVVVDVSHE DPEVKFNWYV  780

781    DGVEVHNAKT KPREEQYNST YRVVSVLTVL HQDWLNGKEY KCKVSNKALP APIEKTISKA  840

841    KGQPREPQVY TLPPSRDELT KNQVSLTCLV KGFYPSRLAV EWESNGQPEN NYKTTPPVLD  900

901    SDGSFFLYSK LTVDKSRWQQ GNVFSCSVMH EALHNHYTQK SLSLSPGK*              949

2Fc hFIX orf in pTK1774 → Lists Single Strand
DNA sequence 2847 bp
R338L hFIX 1-1383 XIa 1384-1446 target First Fc 1447-2127 linker 2128-2163
second Fc 2164-2844
                                                              (SEQ ID NO: 7)
   1    atgcagcgcg tgaacatgat catggccgag agccctggcc tgatcaccat ctgcctgctg   60

61    ggctacctgc tgagcgccga gtgcaccgtg ttcctggacc acgagaacgc caacaagatc  120

121    ctgaaccggc ccaagagata acagcggc aagctggagg agttcgtgca gggcaacctg  180

181    gagagggagt gcatggagga gaagtgcagc ttcgaggagg ccagggaagt gttcgagaac  240

241    accgagcgga ccaccgagtt ctggaagcag tacgtggacg gcgaccagtg cgagagcaac  300
```

-continued

```
 301  ccttgcctga acggcggcag ctgcaaggac gacatcaaca gctacgagtg ctggtgccct   360
 361  ttcggcttcg agggcaagaa ctgcgagctg gacgtgacct gcaacatcaa gaacggccgc   420
 421  tgcgagcagt tctgcaagaa cagcgccgac aacaaagtgg tgtgtagctg caccgagggc   480
 481  tacagactgg ccgagaacca gaagagctgc gagcccgccg tgcccttccc ctgcggcaga   540
 541  gtgagcgtgt cccagaccag caagctgacc agagccgaga ccgtgttccc cgacgtggac   600
 601  tacgtgaata gcaccgaggc cgagaccatc ctggacaaca tcacccagag cacccagtcc   660
 661  ttcaacgact tcaccagagt tgtgggcggc gaggacgcca agcccggcca gttcccctgg   720
 721  caggtggtgc tgaacggcaa agtggatgcc ttctgcggcg gcagcatcgt gaacgagaag   780
 781  tggatcgtga cagccgccca ctgcgtggag accggcgtga agatcaccgt ggtggccggc   840
 841  gaacacaata tcgaggagac cgagcacacc gagcagaagc ggaacgtcat ccggattatc   900
 901  ccccaccaca actacaacgc cgccatcaac aagtacaacc acgacatcgc cctgctggag   960
 961  ctggacgagc tctggtgct gaatagctac gtgacccca tctgcatcgc cgacaaggag  1020
1021  tacaccaaca tcttcctgaa gttcggcagc ggctacgtgt ccggctgggg cagagtgttc  1080
1081  cacaagggca gaagcgccct ggtgctgcag tacctgagag tgcccctggt ggacagagcc  1140
1141  acctgcctgt tgagcaccaa gttcaccatc tacaacaaca tgttctgcgc cggcttccac  1200
1201  gagggcggca gagacagctg ccagggcgac agcggcggac cccacGTGAC AGAGGTGGAA  1260
1261  GGCACCAGCT TTCTGACCGG CATCATCAGC TGGGGCGAGG AATGCGCCAT GAAGGGGAAG  1320
1321  TACGGCATCT ACACCAAGGT GTCCAGATAC GTGAACTGGA TCAAAGAAAA GACCAAGCTG  1380
1381  ACATCTGTGT CTCAGACCTC TAAGCTGACA CGGGCCGAAA CTGTGTTTCC TGATGTGGAC  1440
1441  GGCAGCGACA AGACCCACAC CTGTCCTCCA TGTCCCGCCC CTGAACTGCT GGGCGGACCT  1500
1501  AGCGTGTTCC TGTTCCCCCC AAAGCCCAAG GACACCCTGA TGATCAGCCG GACCCCCGAA  1560
1561  GTGACCTGCG TGGTGGTGGA TGTGTCCCAC GAGGACCCTG AAGTGAAGTT CAATTGGTAT  1620
1621  GTGGATGGCG TGGAAGTGCA CAACGCCAAG ACAAAGCCCA GAGAGGAACA GTACAACTCC  1680
1681  ACCTACCGGG TGGTGTCCGT GCTGACCGTG CTGCACCAGG ACTGGCTGAA TGGCAAAGAG  1740
1741  TATAAGTGCA AAGTGTCCAA CAAGGCCCTG CCTGCCCCCA TCGAGAAAAC CATCAGCAAG  1800
1801  GCCAAGGGCC AGCCCCGCGA ACCCCAGGTG TACACACTGC CCCCTAGCAG GGACGAGCTG  1860
1861  ACCAAGAACC AGGTGTCCCT GACCTGTCTC GTGAAGGGCT TCTACCCTAG CCGGCTGGCC  1920
1921  GTGGAATGGG AGAGCAATGG CCAGCCCGAG AACAATTACA AGACCACCCC CCCTGTGCTG  1980
1981  GACAGCGACG GCTCATTCTT CCTGTACAGC AAACTGACCG TGGACAAGAG CCGGTGGCAG  2040
2041  CAGGGCAATG TGTTCAGCTG TAGCGTGATG CACGAGGCCC TGCACAACCA CTACACCCAG  2100
2101  AAGTCTCTGA GCCTGAGCCC CGGCAAGGGC GGAGGAAGTG GGGGAGGATC TGGCGGCGGC  2160
2161  TCCGATAAGA CACATACCTG CCCCCCTTGC CCTGCCCCAG AGCTGCTGGG AGGCCCTTCT  2220
2221  GTGTTTCTGT TTCCACCTAA GCCTAAAGAT ACACTGATGA TCTCCCGCAC ACCTGAAGTG  2280
2281  ACATGTGTGG TGGTGGACGT GTCACATGAA GATCCAGAAG TGAAGTTTAA TTGGTACGTG  2340
2341  GACGGGGTGG AAGTGCATAA TGCTAAGACC AAACCCCGGG AAGAACAGTA TAACAGCACA  2400
2401  TACAGAGTGG TGTCTGTGCT GACAGTGCTG CATCAGGATT GGCTGAACGG GAAAGAATAC  2460
2461  AAATGTAAAG TGTCTAACAA AGCTCTGCCC GCTCCTATCG AAAAGACAAT CTCCAAGGCT  2520
2521  AAAGGACAGC CCAGAGAACC TCAGGTGTAC ACACTGCCTC CATCCCGCGA CGAGCTGACA  2580
2581  AAAAATCAGG TGTCACTGAC ATGCCTCGTG AAGGGGTTTT ATCCATCTAG GCTGGCTGTG  2640
2641  GAATGGGAAT CCAACGGACA GCCTGAAAAC AACTATAAGA CAACACCTCC CGTGCTGGAC  2700
2701  TCCGATGGCT CATTTTTTCT GTATTCCAAG CTGACTGTGG ATAAGTCCAG ATGGCAGCAG  2760
```

2761 GGAAACGTGT TCTCCTGTTC TGTGATGCAT GAAGCTCTGC ATAATCATTA TACCCAGAAA 2820

2821 AGCCTGTCCC TGTCCCCTGG CAAGTGA                                    2847

TABLE 1

| Amino Acids | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

What is claimed is:

1. A PKR-deficient packaging cell that generates an integration-deficient lentiviral vector that comprises an expression cassette in opposite orientation to LTRs of the vector genome and a self-inactivating 3' U3.

2. The cell of claim 1, wherein the integration-deficient lentiviral vector comprises a polyadenylation signal in opposite orientation to LTRs of the vector genome.

3. The cell of claim 1, wherein the integration-deficient lentiviral vector comprises an internal Pol II promoter in opposite orientation to LTRs of the vector genome.

4. The cell of claim 1, wherein the integration-deficient lentiviral vector comprises an internal Pol III promoter in opposite orientation to LTRs of the vector genome.

5. A method of producing a package cell line with enhanced production of integration-deficient lentiviral vector (IDLV), comprising:

rendering a packaging cell line to lack expression of PKR, introducing an IDLV that comprises an expression cassette in opposite orientation to long terminal repeats (LTRs) of the vector genome and a self-inactivating 3' U3, thereby producing the packaging cell line of claim 1.

* * * * *

UNITED STATES PATENT AND TRADEMARK OFFICE
CERTIFICATE OF CORRECTION

PATENT NO. : 11,560,418 B2
APPLICATION NO. : 15/769252
DATED : January 24, 2023
INVENTOR(S) : Tal Kafri It is certified that error appears in the above-identified patent and that said Letters Patent is hereby corrected as shown below:

In the Specification

Column 18, Line 18: Please correct "Pubin." to read --Publn.--

Column 20, Line 5: Please correct "Fe-Domains" to read --Fc-Domains--

Column 20, Line 22: Please correct "Fe-domains" to read --Fc-domains--

Column 21, Line 6: Please correct "hFIX-Fe" to read --hFIX-Fc--

Column 21, Lines 11-12: Please correct "Fe-domains" to read --Fc-domains--

Column 21, Lines 16-17: Please correct "Fe-domain" to read --Fc-domain--

Column 22, Line 5: Please correct "Fe-Domain" to read --Fc-Domain--

Column 22, Line 21: Please correct "IDLY" to read --IDLV--

Signed and Sealed this
Thirtieth Day of May, 2023

Katherine Kelly Vidal
*Director of the United States Patent and Trademark Office*